US007388078B2

(12) United States Patent
Van Strijp et al.

(10) Patent No.: US 7,388,078 B2
(45) Date of Patent: *Jun. 17, 2008

(54) NUCLEIC ACIDS ENCODING POLYPEPTIDES HAVING CHIPS ACTIVITY

(75) Inventors: Johannes A. G. Van Strijp, NV Odijk (NL); Cornelis P. M. Van Kessel, EX Bunnik (NL); Andreas P. Peschel, Teubingen (DE)

(73) Assignee: Alligator Bioscience AB, Scheelevagen (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/370,574

(22) Filed: Mar. 8, 2006

(65) Prior Publication Data

US 2006/0205655 A1    Sep. 14, 2006

Related U.S. Application Data

(63) Continuation of application No. 10/169,591, filed as application No. PCT/EP01/00270 on Jan. 8, 2001, now Pat. No. 7,018,513.

(30) Foreign Application Priority Data

Jan. 7, 2000    (EP) .................................. 00200068

(51) Int. Cl.
    *C07K 14/00*    (2006.01)
    *A61K 38/00*    (2006.01)
(52) U.S. Cl. .......................................... 530/350; 514/2
(58) Field of Classification Search ................ 530/300, 530/350; 514/2; 424/278.1
    See application file for complete search history.

(56) References Cited

U.S. PATENT DOCUMENTS

| 5,514,555 | A | 5/1996 | Springer et al. |
| 6,839,061 | B1 | 1/2005 | Kamakura et al. |
| 7,081,513 | B2* | 7/2006 | Van Strijp et al. .......... 530/300 |
| 7,153,655 | B2 | 12/2006 | Borrebaeck et al. |
| 2003/0138825 | A1 | 7/2003 | Harayama et al. |
| 2005/0143307 | A1 | 6/2005 | Van Strijp et al. |
| 2006/0019300 | A1 | 1/2006 | Carlsson et al. |
| 2006/0166198 | A1 | 7/2006 | Furebring et al. |

FOREIGN PATENT DOCUMENTS

| EP | 1 095 059 B1 | 5/2001 |
| EP | 1 118 663 A1 | 7/2001 |
| EP | 1 244 790 A0 | 10/2002 |
| EP | 1 586 583 A2 | 10/2005 |
| WO | WO-87/07146 A1 | 12/1987 |
| WO | WO-93/04202 A1 | 3/1993 |
| WO | WO-96/40907 A1 | 12/1996 |
| WO | WO-98/32845 A1 | 7/1998 |
| WO | WO-00/02913 A1 | 1/2000 |
| WO | WO 00/02913 A1 * | 1/2000 |
| WO | WO-01/49711 A2 | 7/2001 |
| WO | WO-02/094868 A2 | 11/2002 |
| WO | WO-03/006048 A1 | 1/2003 |
| WO | WO-2005/100385 A2 | 10/2005 |

OTHER PUBLICATIONS

Haas et al. (2004) N-terminal residues of the chemotaxis inhibitory protein of *Staphylococcus aureus* are essential for blocking formylated peptide receptor but not C5a receptor. J. Immunol. vol. 173, No. 9, pp. 5704-5711.*
Mohuczy et al. (1999) Delivery of antisense DNA by vectors for prolonged effects in vitro and in vivo. Methods Enzymol. vol. 314, pp. 32-51.*
Horii et al. (2000) "The staphylokinase gene is located in the structural gene encoding N-acetylmuramyl-L-alanine amidase in methicillin-resistant *Staphylococcus aureus*", FEMS Microbiol. Lett., vol. 185, No. 2, pp. 221-224.*
U.S. Appl. No. 09/743,861, filed Jan. 17, 2001, Kamakura et al.
U.S. Appl. No. 11/691,745, filed Mar. 27, 2007, Van Strijp et al.
Adang, A.E.P. et al. (Feb. 2, 1994). "Case Histories of Peptidomimetics: Progression From Peptides to Drugs," *Recueil des Travaux Chimiques Pays-Bays* 113:63-78.
Altschul, S.F. et al. (1990). "Basic Local Alignment Search Tool," *J. Mol. Biol.* 215:403-410.
Antal-Szalmas, P. et al. (Jun. 1997). "Quantitation of Surface CD14 on Human Monocytes and Neutrophils," *Journal of Leukocyte Biology* 61:721-728.
Argos, P. (1989). *Protein Structure: A Practical Approach*. T.E. Creighton ed., IRL Press: Oxford, UK, pp. 184-186.
Augustin, J. et al. (1990). "Transformation of *Staphylococcus epidermidis* and Other Staphylococcal Species with Plasmid DNA by Electroporation," *Federation of European Microbiological Societies Microbiology Letters* 66:203-207.
Balasoiu, D. et al. (Mar. 1997). "Granulocyte Function in Women with Diabetes and Asymptomatic Bacteriuria," *Diabetes Care* 20(3):392-395.
Barone F.C. et al. (1999). "Inflammatory Mediators and Stroke: New Opportunities for Novel Therapeutics," *Journal of Cerebral Blood Flow and Metabolism* 19(8):819-834.
Black, M.E. et al. (1996). "Random Sequence Mutagenesis for the Generation of Active Enzymes" Chapter 30 In *Methods in Molecular Biology*, vol. 57; In Vitro Mutagenesis Protocols. M.K. Trower ed., Humana Press, Inc.: Totowa, NJ, pp. 335-349.

(Continued)

*Primary Examiner*—Karen Cochrane Carlson
*Assistant Examiner*—Samuel Wei Liu
(74) *Attorney, Agent, or Firm*—Morrison & Foerster LLP

(57) ABSTRACT

The invention relates to nucleic acid molecules encoding (poly)peptides having chemotaxis inhibiting (poly)peptides CHIPS activity, to recombinant vectors harboring such molecules, and the host cells carrying the vectors. The invention further relates to methods for preparing recombinant (poly) peptides having CHIPS activity and to the use of such recombinant (poly)peptides having CHIPS activity for diagnosis, prophylaxis and treatment, such as the treatment of inflammation reactions and HIV. In addition, the invention provides therapeutic and diagnostic compositions comprising as the active ingredient the (poly)peptide having CHIPS activity.

5 Claims, 14 Drawing Sheets

OTHER PUBLICATIONS

Brosius, J. (1984). "Toxicity of an Overproduced Foreign Gene Product in *Escherichia coli* and its Use in Plasmid Vectors for the Selection of Transcription Terminators," *Gene* 27:161-172.

Bruckner, R. (1992). "A Series of Shuttle Vectors for *Bacillus subtilis* and *Escherichia coli,*" *Gene* 122:187-192.

Byrne, J.G. et al. (Dec. 1992). "Complete Prevention of Myocardial Stunning, Contracture, Low-Reflow, and Edema After Heart Transplantation by Blocking Neutrophil Adhesion Molecules During Reperfusion," *The Journal of Thoracic Cardiovascular Surgery* 104(6):1589-1596.

Cadwell, R.C. et al. (1992). "Randomization of Genes by PCR Mutagenesis," *PCR Methods and Applications* 2:28-33.

Cho, C.Y. et al. (Sep. 3, 1993). "An Unnatural Biopolymer," *Science* 261:1303-1305.

Cooper, Jr., J.A.D. et al. (1994). "Alteration of Cellular Cytosolic Calcium and Chemotactic Peptide Binding by an Inhibitor of Neutrophil Function," *Am. J. Physiol. Cell. Mol. Physiol.* 11:L71-78.

Cooper, Jr., J.A.D. et al. (1996). "Characterization of a Neutrophil Inhibitor Peptide Harvested From Human Bronchial Lavage: Homology to Influenza a Nucleoprotein," *American Journal of Respiratory Cell and Molecular Biology* 15:207-215.

Cox, G. (Jul./Aug. 1998). "The Role of Neutrophils in Inflammation," *Can. Respir. J.* 5(Suppl. A):37A-40A.

Creighton, T.E. *Proteins: Structures and Molecular Principles* W.H. Freeman and Company New York, pp. 314-315, 1990.

de Bont, D.B.A. et al. (1996). "Molecular Diversity of Peptidomimetics: Approaches to the Solid-Phase Synthesis of Peptidosulfonamides," *Bioorganic & Medicinal Chemistry* 4(5):667-672.

de Bont, D.B.A. et al. (1996). "Solid-Phase Synthesis of Peptidosulfonamide Containing Peptides Derived From Leu-Enkephalin," *Bioorganic & Medicinal Chemistry Letters* 6(24):3035-3040.

de Haas, C.J.C. et al. (1998). "A Synthetic Lipopolysaccaride-Binding Peptide Based on Amino Acids 27-39 of Serum Amyloid P Component Inhibits Lipopolysaccharide-Induced Responses in Human Blood," *The Journal of Immunology* 161:3607-3615.

de Haas, C.J.C. et al. (1998). "Affinities of Different Proteins and Peptides for Lipopolysaccharide as Determined by Biosensor Technology," *Biochemical and Biophysical Research Communications* 252(2):492-496.

de Haas, C.J.C. et al. (Mar. 1, 2004). "Chemotaxis Inhibitory Protein of *Staphylococcus aureus*, a Bacterial Antiinflammatory Agent,"*J. Exp. Med.* 199(5);687-695.

de Velasco, E.A. et al. (Mar. 1994). "Epitope Specificity of Rabbit Immunoglobulin G (IgG) Elicited by Pneumococcal Type 23F Synthetic Oligosaccharide- and Native Polysaccharide-Protein Conjugate Vaccines: Comparison with Human Anti-Polysaccharide 23F IgG," *Infection and Immunity* 62(3):799-808.

Demling, R.H. (1995). "The Modern Version of Adult Respiratory Distress Syndrome," *Ann. Rev. Med.* 46:193-202.

Edwards, S.W. et al. (Jul. 1997). "Seeing the Wood for the Trees: The Forgotten Role of Neutrophils in Rheumatoid Arthritis," *Immunology Today* 18(7):320-324.

Erich, T. et al. (Dec. 15, 1989). "Binding Characteristics and Cross-Reactivity of Three Different Antilipid A Monoclonal Antibodies," *The Journal of Immunology* 143(12):4053-4060.

Fahey, J.L. et al. (1992). "Status of Immune-Based Therapies in HIV Infection and AIDS," *Clin. Exp. Immunol.* 88:1-5.

Foster, T.J. (Dec. 2005). "Immune Evasion by Staphylococci," *Nature Reviews Microbiology* 3:948-958.

Fox, J.L. (Dec. 12, 1994). "AIDS Product Development Follows its Own Rules," *Biotechnology* 12:1329-1331.

Fujishima, S. et al. (1995). "Neutrophil-Mediated Tissue Injury and its Modulation," *Intensive Care Med.* 21:277-285.

Gallop, M.A. et al. (Apr. 29, 1994). "Applications of Combinatorial Technologies to Drug Discovery. 1. Background and Peptide Combinatorial Libraries," *Journal of Medicinal Chemistry* 37(9):1233-1251.

Gante, J. (1994). "Peptidomimetics—Tailored Enzyme Inhibitors," *Angew. Chem. Int. Ed. Engl.* 33:1699-1720.

Gennari, C. et al. (1998). "Synthesis of Combinatorial Libraries of Vinylogous Sulfonamidopeptides (vs-Peptides)," *Eur. J. Org. Chem.* pp. 2437-2449.

Giannis, A. et al. (1993). "Peptidomimetics for Receptor Ligands—Discovery, Development, and Medical Perspectives," *Angew. Chem. Int. Ed. Engl.* 32:1244-1267.

Goddard, T.D. et al. "Sparky—NMR Assignment and Integration Software," located at <http://www.cgl.ucsf.edu/home/sparky> visited on Nov. 23, 2006. (3 pages).

Gordon, E.M. et al. (May 13, 1994). "Applications of Combinatorial Technologies to Drug Discovery. 2. Combinatorial Organic Synthesis, Library Screening Strategies, and Future Directions," *Journal of Medicinal Chemistry* 37(10):1385-1401.

Haas, P.J. et al. (2004). "N-Terminal Residues of the Chemotaxis Inhibitory Protein of *Staphylococcus aureus* Are Essential for Blocking Formylated Peptide Receptor but Not C5a Receptor," *The Journal of Immunology* 173:5704-5711.

Hass, P.J. et al. (2005). "The Structure of the C5a Receptor-Blocking Domain of Chemotaxis Inhibitory Protein of *Staphylococcus aureus* is Related to a Group of Immune Evasive Molecules," *J. Mol. Biol.* 353:859-872.

Han, H. et al. (Mar. 20, 1996). "Azatides: Solution and Liquid Phase Syntheses of a New Peptidomimetic," *Journal of the American Chemical Society* 118(11):2539-2544.

Heller, T. et al. (1999). "Selection of a C5a Receptor Antagonist From Phage Libraries Attenuating the Inflammatory Response in Immune Complex Disease and Ischemia/Reperfusion Injury," *The Journal of Immunology* 163:985-994.

Hiemstra, P.S. et al. (1998). "Neutrophil Serine Proteinases and Defensins in Chronic Obstructive Pulmonary Disease: Effects on Pulmonary Epithelium," *European Respiratory Journal* 12:1200-1208.

Ho, S.N. et al. (1989). "Site-Directed Mutagenesis by Overlap Extension Using the Polymerase Chain Reaction," *Gene* 77:51-59.

Horii, T. et al. (2000). "The Staphylokinase Gene is Located in the Structural Gene Encoding N-Acetylmuramyl-L-Alanine Amidase in Methicillin-Resistant *Staphylococcus aureus,*" *Federation of European Microbiological Societies Microbiology Letters* 185:221-224.

Invitrogen Corporation. (Jun. 16, 2006). *EnterokinaseMax (EKMax) User Manual*, version H, pp. 1-8.

Invitrogen Corporation. (Date Unknown). *EK-Away Resin User Manual*, pp. 1-4.

Invitrogen Corporation. (Date Unknown). *ProBond abd Bi-NTA Resin User Manual*, pp. 1-19.

Invitrogen Corporation. (Date Unknown). p*TrcHis 2Xpress Vector User Manual*, one page.

Jean, W.C. et al. (Dec. 1998). "Reperfusion Injury After Focal Cerebral Ischemia: The Role of Inflammation and the Therapeutic Horizon," *Neurosurgery* 43(6):1382-1396.

Kruijtzer, J.A.W. et al. (1995). "Synthesis in Solution of Peptoids Using Fmoc-Protected N-Substituted Glycines," *Tetrahedron Letters* 36(38):6969-6972.

Kruijtzer, J.A.W. et al. (1997). "Approaches to the Synthesis of Ureapeptoid Peptidomimetics," *Tetrahedron Letters* 38(30):5335-5338.

Kruijtzer, J.A.W. et al. (1998). "Solid-Phase Syntheses of Peptoids Using Fmoc-Protected N-Substituted Glycines: The Synthesis of (Retro) Peptoids of Leu-Enkephalin and Substance P," *Chem. Eur. J.* 4(8):1570-1580.

Lin, P. et al. (1998). "Solid-Phase Synthesis of Peptidomimetic Oligomers with a Phosphodiester Backbone," *Bioorganic & Medicinal Chemistry Letters* 8:511-514.

Liskamp, R.M.J. (1994). "A New Application of Modified Peptides and Peptidomimetics: Potential Anticancer Agents," *Angew. Chem. Int. Ed. Engl.* 33(3):305-307.

Liskamp, R.M.J. (Jan. 1, 1994). "Conformationally Restricted Amino Acids and Dipeptides, (Non) Peptidomimetics and Secondary Structure Mimetics," *Recueil des Travaux Chimiques des Pays-Bas* 113:1-19.

Liskamp, R.M.J. (1994). "Opportunities for New Chemical Libraries: Unnatural Biopolymers and Diversomers," *Angew. Chem. Int. Ed. Engl.* 33(6):633-636.

Marmur, J. (1961). "A Procedure for the Isolation of Deoxyribonucleic Acid From Micro-Organisms," *J. Mol. Biol.* 3:208-218.

McPherson, M.J. (1991). *Directed Mutagenesis A Practical Approach*. Oxford University Press: Oxford, pp. xi-xvii. (Table of Contents).

Moos, W.H. et al. (1993). "Recent Advances in the Generation of Molecular Diversity" Chapter 33 *In Annual Reports in Medicinal Chemistry* 28:315-324.

Moree, W.J. et al. (1991). "Peptides Containing a Sulfinamide or a Sulfonamide Moiety: New Transition-State Analogues," *Tetrahedron Letters* 32(3):409-412.

Moree, W.J. et al. (1992). "Synthesis of Peptides Containing the Beta-Substituted Aminoethane Sulfinamide or Sulfonamide Transition-State Isotere Derived From Amino Acids," *Tetrahedron Letters* 33(42):6389-6392.

Moree, W.J. et al. (1993). "Synthesis of Peptides Containing a Sulfinamide or a Sulfonamide Transition-State Isostere," *Tetrahedron* 49(5):1133-1150.

Moree, W.J. et al. (1995). "Synthesis of Peptidosulfinamides and Peptidosulfonamides: Peptidomimetics Containing the Sulfinamide or Sulfonamide Transition-State Isostere," *J. Org. Chem.* 60(16):5157-5169.

Nosoh, Y. et al. (1991). "Concluding Remarks" Chapter 7 *In Protein Stability and Stabilization Through Protein Engineering*. Ellis Horwood Limited, pp. 197-217.

Olson, G.L. et al. (Oct. 15, 1993). "Concepts and Progress in the Development of Peptide Mimetics," *Journal of Medicinal Chemistry* 36(21):3039-3049.

Paikoff, S.J. et al. (1996). "The Solid Phase Synthesis of N-Alkylcarbamate Oligomers," *Tetrahedron Letters* 37(32):5653-5656.

Peschel, A. et al. (Mar. 26, 1999). "Inactivation of the dlt Operon in *Staphylococcus aureus* Confers Sensitivity to Defensins, Protegrins, and Other Antimicrobial Peptides," *The Journal of Biological Chemistry* 274(13):8405-8410.

Pillinger, M.H. et al. (Aug. 1995). "The Neurophil in Rheumatoid Arthritis," *Rheumatic Disease Clinics of North America* 21(3):691-714.

Postma, B. et al. (2004). "Chemotaxis Inhibitory Protein of *Staphylococcus aureus* Binds Specifically to the C5a and Formylated Peptide Receptor," *The Journal of Immunology* 172:6994-7001.

Postma, B. et al. (Jan. 21, 2005). "Residues 10-18 Within the C5a Receptor N Terminus Compose a Binding Domain for Chemotaxis Inhibitory Protein of *Staphylococcus aureus*," *The Journal of Biological Chemistry* 280(3):2020-2027.

Rooijakkers, S.H.M. et al. (2005). "Anti-Opsonic Properties of Staphylokinase," *Microbes and Infection* 7:476-484.

Rooijakkers, S.H.M. et al. (Sep. 2005). "Immune Evasion by a Staphylococcal Complement Inhibitor That Acts on C3 Convertases," *Nature Immunology* 6(9):920-927.

Rooijakkers, S.H.M. et al. (Dec. 2005). "Staphylococcal Innate Immune Evasion," *Trends in Microbiology* 13(12):596-601.

Sahu, A. et al. (2000). "Complement Inhibitors: A Resurgent Concept in Anti-inflammatory Theraputics," *Immunopharmacology* 49:133-148.

Shine, J. et al. (Apr. 1974). "The 3'-Terminal Sequence of *Escherichia coli* 16S Ribosomal RNA: Complementarity to Nonsense Triplets and Ribosome Binding Sites," *Proc. Nat. Acad. Sci. USA* 71(4):1342-1346.

Simon, R.J. et al. (Oct. 1992). "Peptoids: A Modular Approach to Drug Discovery," *Proc. Natl. Acad. Sci. USA* 89:9367-9371.

Smith, III, A.B. et al. (1992). "Design, Synthesis, and Crystal Structure of a Pyrrolinone-Based Peptidomimetic Possessing the Conformation of a Beta-Strand: Potential Application to the Design of Novel Inhibitors of Proteolytic Enzymes," *J. Am. Chem. Soc.* 114(26):10672-10674.

Sommerfield, T. et al. (1995). "Synthesis of Psi[SCH2]-, Psi[SOCH2]-, and Psi[SO2CH2]-Peptide Isosters," *Angew. Chem. Int. Ed. Eng.* 34(5):553-554.

Troelstra, A. et al. (Feb. 1997). "Dual Effects of Soluble CD14 on LPS Priming of Neutrophils," *Journal of Leukocyte Biology* 61:173-178.

Troelstra, A. et al. (Jun. 1997). "Saturable CD14-Dependent Binding of Fluorescein-Labeled Lipopolysaccharide to Human Monocytes," *Infection and Immunity* 65(6):2272-2277.

Tunkel, A.R. et al. (Apr. 1993). "Pathogenesis and Pathophysiology of Bacterial Meningitis," *Clinical Microbiology Reviews* 6(2):118-136.

Tuomanen, E.I. (1996). "Molecular and Cellular Mechanisms of Pneumococcal Meningitis," *Annals New York Academy of Sciences* 797:42-52.

van Ameijde, J. et al. (2000). "Peptidomimetic Building Blocks for the Synthesis of Sulfonamide Peptoids," *Tetrahedron Letters* 41:1103-1106.

van Kessel, K. et al. (2003). "Tips and Tricks From *Staphylococcus aureus*," *Tropical Disease From Molecule to Bedside, Advances in Experimental Medicine and Biology*, S. Marzuki et al. eds. 531:341-349.

Veldkamp, K.E. et al. (1997). "Staphylococcal Culture Supernates Stimulate Human Phagocytes," *Inflammation* 21(5):541-551.

Veldkamp, K.E. et al. (Oct. 2000). "Modulation of Neutrophil Chemokine Receptors by *Staphylococcus aureus* Supernate," *Infection and Immunity* 68(10):5908-5913.

Veldkamp, K.E. et al. "139-G. Slide Session Phagocytosis: Abstract G-64. A Novel Neutrophil-Chemotoxins Inhibitory Protein of *Staphylococcus aureas*," 38th *Annual ICAAC*: San Diego, CA p. 302, 1998.

Veldkamp, K.E. et al. "Abstract D-57. Specific Downregulation of Neutrophil Chemotaxis by Staphylococcal Culture Supernates," *Abstracts in General Medical Microbiology* p. 217, 1998.

von Heijne, G. (1986). "A New Method for Predicting Signal Sequence Cleavage Sites," *Nucleic Acids Research* 14(11):4683-4690.

Wilson, M.E. et al. (1998). "An Efficient Synthesis of N,N'-Linked Oligoureas," *Tetrahedron Letters* 39:6613-6616.

Zhou, Y. et al. (1991). "Random Mutagenesis of Gene-Sized DNA Molecules by Use of PCR with Taq DNA Polymerase," *Nucleic Acids Research* 19(21):1 page.

Zuckerman, R.N. et al. (1994). "Discovery of Nanomolar Ligands for 7-Transmembrane G-Protein-Coupled Receptors From a Diverse N-(Substituted) Glycine Peptoid Library," *Journal of Medicinal Chemistry* 37(17):2678-2685.

\* cited by examiner

```
  1  ATAAATTTAAATATAGAATTTAAGGAGAATTAACATCATTATGAAAAAGAAATTAGCAACAACAGTTT
 69  TAGCATTAAGTTTTTTAACGGCAGGAATCAGTACACACCATCATTCAGCGAAAGCTTTTACTTTTGAA
                                             T
137  CCGTTTCCTACAAAATGAAGAGAAATAGAATCAAATAAGAGAAAATGTTTAGAGAAAGAAAAAGCTTATAAAGA
                                 A
205  ATCATTTAAAAATAGTGGTCTTCCTACAACGCTAGGAAAAATTAGATGAACGTTTGAGAAATTATTTAA
273  AGAAAGGCACAAAAAATTCTGCTCAATTTGAAAAAAAATGGTTATTTTAACTGAAAATAAAGGTTACTAT
                                                                      T
341  ACAGTATATCTGAATACACCACTTGCTGAAGATAGAAAAAATGTTGAGTTACTAGGTAAAAATGTATAA
409  AACATACTTCTTTAAAAAGGAGAGTCTAAATCATCTTATGTAATTAATGGTCCTGGAAAAACTAATG
                                            C
477  AATATGCATACTAATAGTAGTTACATAAATTAAAAGGTAGATATTTCTTTTTATATAAAGGTTTGGC
545  AGACATTTCATAACTTGCCAAACCTTTATATATATCTAATTATCAAACTGCACTAAACTT

SEQ ID NO: 4
```

Fig. 4.

FTFEPFPTNEEIESNKKMLEKEKAYKESFKNSGLPTTLGKL

DERLRNYLKKGTKNSAQFEKMVLTENKGYYTVYLNTPL

AEDRKNVELLGKMYKTYFFKKGESKSSYVINGPGKTNEYAY

SEQ ID NO: 5

Fig. 5.

1. S.aureus Newman
2. S.aureus Newman
3. S.aureus Col
4. S.aureus Col
5. S.aureus 1690
6. S.aureus 1690

NUCLEIC ACIDS ENCODING POLYPEPTIDES HAVING CHIPS ACTIVITY

CROSS REFERENCE TO RELATED APPLICATIONS

This application is a continuation Application of U.S. patent application Ser. No. 10/169,591 (now U.S. Pat. No. 7,018,513), filed Jan. 16, 2003, which is a 371 of PCT/EP01/00270 filed Jan. 8, 2001, which claims the benefit of EP 00200068.5, filed Jan. 7, 2000, the disclosures of which are hereby incorporated by reference in their entirety.

BACKGROUND OF THE INVENTION

The present invention relates to a nucleic acid molecule encoding a (poly)peptide having chemotaxis inhibitory protein (CHIPS) activity. The invention further relates to the use of the information contained in the nucleic acid for the preparation of the corresponding (poly)peptide and to vectors and hosts for use therein. The invention in addition relates to non-(poly)peptide molecules having a similar structure and function as the (poly)peptides. The (poly)peptide having CHIPS activity that is encoded by the nucleic acid molecule of the invention can be used in the treatment of inflammation reactions. The (poly)peptides and non-(poly)peptides can in addition be used for inhibiting activation of leukocytes and endothelial cells.

Leukocytes are mainly involved in protecting the body against foreign invaders (e.g. bacteria, viruses, fungi, and cancer cells). The most important cells are lymphocytes, monocytes and neutrophils. Lymphocytes form the specific immune system and cause immune reactions against invaders. Their most important task is to build up specific memory against the invader, so that the next time the invader enters the body it is recognized, killed, and removed rapidly. Sometimes these lymphocytes not only attack invaders, but also react against certain structures and/or molecules ( )so-called auto-antigens) of the own body, causing auto-immune diseases (e.g. rheumatoid arthritis). Killing and removal of invaders is mostly done by monocytes and neutrophils, cells of the innate immune system, by direct recognition of the invaders or with the help of specific lymphocytes.

In contrast to the delicate network of the fine-tuned and controlled reactions of lymphocytes, cells of the innate system react in a relatively non-specific and aggressive way. Since they are part of the body's first line of defense, their most important task is to kill and remove the invading agent as quickly as possible. This is accomplished through very aggressive substances (e.g. free radicals and enzymes) that are not only lethal to the invader, but also cause damage to host cells in the vicinity. Substances from these damaged cells and the locally activated cells from the innate system itself will further attract increasing numbers of neutrophils and monocytes, causing local inflammation. In most cases, such an aggressive and damaging inflammatory reaction, caused by over activated neutrophils, is unnecessary. In some cases this inflammatory response is responsible for serious, sometimes lethal disorders and includes conditions like Adult Respiratory Distress Syndrome (ARDS), severe tissue damage following thrombotic events such as heart attacks and stroke, inflammatory bowel diseases and rheumatoid arthritis. The inflammation will subside once all the invaders have been killed and removed, together with the various cells killed in the process. Healing of the wound, caused by the inflammatory response, can then begin.

Although there is some overlap in function, the main task of neutrophils is to attack the invaders and the main task of monocytes is to remove the debris resulting from this attack. In addition, neutrophils have another peaceful task in assisting the wound healing process.

When bacteria have invaded the body and, for example, infected the central nervous system (as in meningitis) they start to produce microbial substances, including the formylated polypeptides, such as, for example, the formyl-methionyl-leucyl-phenylalanine (fMLP) peptide. Other substances of microbial origin activate the complement factor 5 (C5) convertase enzyme-complex, that converts C5 of the complement system into its activated C5a form. Both C5a and fMLP are chemo-attractants: substances that can activate and attract cells from the blood vessels (the migration process). Neutrophils are responsive to these two substances and also to interleukin-8 (IL-8). This "chemokine" (the name given to chemo-attractants that are produced by cells of the immune system) is produced mainly by activated monocytes (but also in minute amounts by the activated neutrophils themselves). Neutrophils interact with these substances, because they have receptors for these substances on the outside of their cell membrane.

Activated neutrophils can easily migrate from blood vessels. This is because the chemo-attractants, microbial products and substances from activated monocytes will have increased the permeability of the vessels and stimulated the endothelial cells of the vessel walls to express certain adhesion molecules. Neutrophils express selectins and integrins (e.g. CD11b/CD18) that bind to these adhesion molecules. Once the neutrophil has adhered to the endothelial cells, it is able to migrate through the cells, under the guidance of chemo-attractants/chemokines, towards the site of infection, where the concentration of these substances is at its highest. These substances also activate neutrophils to produce a range of other molecules, some of which attract more neutrophils (and subsequently monocytes), but mostly, they are responsible for destroying the invading bacteria. Some of these substances (e.g. free radicals, enzymes that break down proteins (proteases) and cell membranes (lipase) are so reactive and non-specific that cells from the surrounding tissue (and the neutrophils themselves) are destroyed, causing tissue damage. This damage is exacerbated by the presence of blood derived fluid which has transgressed the leaky vessel wall and is responsible for the swelling that always accompanies inflammation (called oedema). The pressure build up caused by this excess fluid results in further cell damage and death.

Later in the inflammatory process, monocytes migrate to the scene and become activated. Besides their role in removing bacteria and cell debris, they also produce substances such as tumour necrosis factor (TNF) and IL-8, which in turn attract more activated eutrophils, causing further local damage. TNF also has a direct stimulatory effect on neutrophils. Once all the invaders have been removed, the inflammatory response will subside and the area will be cleared of the remaining 'casualties'. Then the process of wound healing starts. Although it is known that neutrophils play a pivotal role in wound healing, it is not clear which neutrophil-derived substances are involved and how the neutrophils are active in healing without being aggressive to the surrounding tissue. In general, damaged tissue will be replaced by scar tissue formed mainly of fibroblasts and collagen. When inflammation occurs in areas of the body with an important function, like tissues formed from heart muscle cells, brain cells or lung alveolar cells, normal function will be compromised by the resulting scar formation, causing serious conditions like heart failure, paralysis and emphysema. To minimise the debilitating consequences of these conditions, it is important to 'dampen' the inflammatory reaction as quickly as possible.

Intervention to control the acute early phase inflammatory response presents an opportunity to improve the prognosis for a wide range of patients whose symptoms can be traced back to such an event. Such an approach has been advocated for many acute and chronic inflammation-based diseases and shown to have potential based on findings from relevant disease models. Classical anti-inflammatory drugs such as steroids and Non Steroid Anti-Inflammatory Drugs (NSAIDS) do not have the ideal profile of action, either in terms of efficacy or safety. Steroids affect the 'wrong' cell type (monocytes) and their dampening effects are easily bypassed. NSAIDS generally show a relatively mild effect partly because they intervene at a late stage in the inflammatory process. Both classes of drugs produce a range of undesirable side effects resulting from other aspects of their pharmacological activity. Drugs acting directly and specifically to prevent migration and activation of neutrophils may have a number of advantages. Several drugs under early development only interfere with one individual aspect of neutrophil activation (e.g. C5 convertase inhibitors, antibodies against C5a, C5a-receptor blocking drugs) and migration (antibodies against integrins (like CD11b/CD18) and L-selectin on neutrophils and antibodies against adhesion molecules (like ICAM-1 and E-selectin) on endothelial cells). Antibodies against TNF and IL-8 have effects in chronic inflammation, but only marginal effects in acute inflammation, because of the minimal role monocytes (which are mainly responsible for these substances' production) play in the acute phase.

Sometimes, the cause of the acute inflammation cannot be removed and the inflammation becomes chronic. With the exception of tuberculosis, chronic hepatitis and certain other conditions, this is seldom the case with infections. However, chronic inflammation can also be caused by stimuli other than bacteria, such as auto-immune reactions. Research has shown that in chronic inflammation the role of monocytes is much more prominent, and that neutrophil migration and activation, monocyte migration and activation, tissue damage, removal of dead cells and wound healing are all going on at the same time. This complex cascade of interactions between cells and many different cytokines and chemokines has been the subject of intensive research for many years. It was believed that monocytes and their products were the most important elements that needed to be inhibited to dampen chronic inflammation. This explains why steroids, which specifically interact with monocytes, are generally more effective in chronic as opposed to acute inflammation. Long-term treatment with steroids however, is not a desirable option, because severe and unacceptable side effects can occur at the doses required to produce a clinical effect. Newer treatments using antibodies against TNF or IL-8 have shown good results, and were initially seen as proof of the major role monocytes were thought to play in chronic inflammation. Recent research casts doubts on an exclusive role for monocytes in inflammation and points to a critical role for neutrophils, which are now seen to represent better targets for therapeutic intervention.

The underlying cause of a chronic inflammatory condition is not always clear, and the original cause may not always be responsible for future recurrence. Some scientists believe that in certain chronic inflammatory diseases there is a continuous cycle of events. Their idea is that existing activated neutrophils and monocytes continuously attract and activate new groups of cells, thus perpetuating the inflammatory response even when the initial stimulus is no longer present. This would suggest that an acute or periodic treatment with an effective inhibitor of the neutrophil and monocyte activation would stop the cycle of new cell recruitment, leading in due course to modification of disease progression, or even a complete cure, and not just symptomatic relief.

In the research that led to the present invention a new agent with inflammation-inhibiting properties was found in the extracellular medium of growing *Staphylococcus aureus* (*S. aureus*). This agent is the subject of co-pending application PCT/NL99/00442. The agent was found to be capable of directly or indirectly blocking different chemokine receptors. Incubation of different cells with the medium resulted in a greatly reduced expression of a number of the chemokine receptors, both of the expression of receptors of classical chemotactic agents such as fMLP and C5a on granulocytes and of the expression of CXCR4 and CCR5 receptors on lymphocytes, monocytes and macrophages. The reduced receptor expression was related to greatly reduced chemotaxis relative to the chemokines, as well as a reduced infection with HIV.

The activity of the protein is already manifest in the culture supernatant of the growing *S. aureus*. The active protein could be further purified, for example by means of a number of Ligand Dye columns. A pre-purification was first performed on a so-called "yellow columm" ("Reactive Yellow 86" ligand dye cross-linked 4% beaded agarose column (Sigma)), followed by an absorption chromatography column (the so-called "green column" ("Reactive Green 19" ligand dye cross-linked 4% beaded agarose column (Sigma)) and a DNA column (DNA Cellulose (Pharmacia)). Both latter columns can be interchanged. The DNA column removes a contaminant with the same molecular weight as the protein. The absorption chromatography column concentrates the protein and is selective for the protein. Finally, a post-purification also takes place by means of gel filtration and anion exchange chromatography (MonoQ, Pharmacia). In the gel filtration the protein with the molecular weight of about 17 kDa is selected. This is the protein that was found to have chemotaxis inhibitory properties. Because this protein is isolated from the supernatant of the *Staphylococcus aureus* and gives inhibition of chemotaxis, this protein was named "CHIPS": CHemotaxis Inhibitory Protein from *Staphylococcus aureus* (herein also referred to as the "original CHIPS").

Isolation of the CHIPS protein out of the supernatant of *S. aureus* is not very cost-effective. In addition, it is desirable for the practical use of CHIPS in therapy that the active part of the protein is isolated. Smaller protein or peptide molecules have a reduced risk of inducing an immunological response in a subject receiving the protein or peptide for therapy. Furthermore, it is desirable to be able to modify the protein or peptide to further increase the biological activity and/or lower the immunogenicity thereof.

It is therefore the object of the present invention to provide the means for producing the original CHIPS protein or other corresponding (poly)peptides that have CHIPS activity, as well as functional fragments, derivatives or analogues thereof other than by isolation from the natural producing host cell.

DETAILED DESCRIPTION OF THE PREFERRED EMBODIMENTS

The present invention therefore provides a nucleic acid molecule comprising a nucleotide sequence encoding a (poly)peptide having CHIPS activity, said nucleotide sequence corresponding to a sequence being selected from the group consisting of:

a) a nucleotide sequence comprising at least part of the sequence as depicted in FIG. 4 (SEQ ID NO 4);

b) nucleotide sequences encoding a (poly)peptide having CHIPS activity and having the amino acid sequence depicted in FIG. 5 (SEQ ID NO 5);

c) nucleotide sequences encoding a (poly)peptide having CHIPS activity and having at least one portion of the amino acid sequence depicted in FIG. 5 (SEQ ID NO 5);

d) nucleotide sequences being at least 40% identical to any one of the nucleotide sequences a), b) or c);

e) nucleotide sequences hybridizing at stringent conditions with any one of the nucleotide sequences a), b), c) or d), and f) nucleotide sequences complementary to any of the nucleotide sequences a), b), c), d) or e).

Regarding the identity or homology as mentioned under d) it should be noted that for gapped alignments, statistical parameters can be estimated using the Smith-Waterman algorithm that produces optimal alignment scores. Homologues of the CHIPS nucleic acid sequence or protein sequence are defined by a Gap Open Penalty of at least 12 and a Gap Expression Penalty of at least 1.

"CHIPS activity" is herein defined as the ability to specifically impair at least the responses induced by both fMLP and C5a, including at least impairment of ligand-(C5a or fMLP) binding, and optionally impairment of chemotaxis and cell-activation (e.g. calcium mobilization). However, the (poly)peptides may in addition have other biological activities, such as an inhibitory effect on the activation of leukocytes and endothelial cells.

In the description that follows the terms "CHIPS protein" and "CHIPS gene" or "chp gene" are used for the protein isolated from the supernatant of naturally occurring *S. aureus*, and its isolated gene, respectively. "(Poly)peptide having CHIPS activity" and "nucleic acid molecule encoding a (poly)peptide having CHIPS activity" are used for all other corresponding (poly)peptides and nucleic acid molecules that are in some way related to or derived from the CHIPS protein or gene but have an amino acid or nucleotide sequence that is not identical thereto. The CHIPS activity as defined above is an inherent feature of the present (poly)peptides. This effect will been demonstrated for the CHIPS protein in Example 5.

The sequence as given in FIG. 4 (SEQ ID NO 4) is the DNA sequence as isolated according to the invention. It comprises a promoter region from nucleotides 1 to 40, a leader peptide sequence from nucleotides 41 to 124, the coding region for the (poly)pep tide having CHIPS activity from nucleotide 125 to 490, as well as a 3' untranslated region from nucleotides 491 to 603.

In a first embodiment of the invention, the isolated nucleic acid molecule has a nucleotide sequence which corresponds to nucleotides 1 to 490 of FIG. 4. In an alternative embodiment the promoter region is no longer present. In this embodiment the nucleotide sequence of the nucleic acid molecule corresponds to nucleotides 41 to 490 of FIG. 4. With this nucleic acid molecule a different promoter and/or other transcription regulatory sequences can be used. The choice of a promoter and/or other regulatory sequences depends on the conditions under which transcription is to take place. The skilled person is capable of selecting suitable promoter and/or other transcription regulatory regions.

The isolated CHIPS gene of FIG. 4 or any nucleic acid derived therefrom may for example be operably linked to the trc expression system (Brosius et al., Gene 27: 161-172 (1984)). Many other suitable expression control sequences and methods of expressing recombinant proteins are known (F. M. Ausubel et al., Current Protocols in Molecular Biology, John Wiley and Sons, Inc., New York, N.Y.).

The nucleotide sequence as given in FIG. 4 also contains a leader peptide sequence. The coding region of the mature protein corresponds to nucleotides 125 to 490 of FIG. 4. Other leader sequences can be used. Or the leader sequence may be omitted entirely, depending on the host cell in which the sequence is to be expressed.

The amino acid sequence in FIG. 5 is deduced from the DNA sequence in FIG. 4. In a further embodiment of the invention the nucleic acid molecule thus may have a nucleotide sequence that corresponds to all degenerate variants of the isolated CHIPS gene.

The invention furthermore relates to nucleic acid molecules that encode (poly)peptides that do not have the complete sequence of FIG. 5 but one or more functional portions thereof that in themselves or together constitute a biologically active (poly)peptide having CHIPS activity. Such portions may vary in size from the complete amino acid sequence minus one amino acid to peptides of at least 2, preferably at least 5 amino acids. In case the active part of the protein lies in two or more portions of the complete amino acid sequence, the invention also relates to nucleic acid sequences encoding these separate portions in a manner that leads to a peptide configuration that retains the biological activity. In practice this can for example mean that spacer sequences are to be incorporated in between biologically active portions to lead to a biologically active conformation.

Thus, when reference is made to "at least part of the sequence" this means not only the three parts described above (i.e. nucleotides 1-490, 41-490 and 125-490) but also other fragments of the gene or combinations thereof provided that they still encode a (poly)peptide having CHIPS activity.

In a further embodiment thereof, the invention thus provides an isolated nucleic acid molecule of the invention which consists of the coding region of one or more portions of the amino acid sequence of FIG. 5, wherein one portion of the amino acid sequence constitutes alone or with other portions of the amino acid sequence the region(s) of the (poly)peptide having CHIPS activity that lead to biological activity.

The present invention is not limited to nucleic acid molecules having the exact same sequence as the sequence depicted in FIG. 4 or the above described variants thereof. Therefore, according to the invention additional nucleic acid molecules are provided having a nucleotide sequence which is at least 40%, preferably at least 50%, more preferably at least 60%, even more preferably at least 70%, most preferably at least 80%, and the most preferably at least 90% identical to any one of the nucleotide sequences as defined under a), b) or c) above.

It was found that CHIPS is less than 40% homologous to proteins and peptides known to date. Proteins and peptides that show at least 40% amino acid homology to the CHIPS protein and have CHIPS activity are thus also part of this invention.

The invention further relates to nucleic acid molecules having a nucleotide sequence hybridising under stringent conditions with a nucleic acid molecule corresponding with the nucleotide sequence given in FIG. 4 or degenerate sequences thereof, which encode an amino acid sequence as given in FIG. 5. Stringent conditions are constituted by overnight hybridisation at 42° C. in 5×SSC (SSC=150 mM NaCl, 15 mM trisodium citrate) and washing at 65° C. at 0.1×SSC. In addition to 5×SSC the hybridisation solution may comprise 50% formamide, 50 mM sodium phosphate (pH 7.6), 5× Denhardt's solution, 10 dextran sulphate and 20 µg/ml denatured sheared salmon sperm DNA.

The invention is also not limited to the gene which encodes the (poly)peptide having CHIPS activity, but also relates to nucleic acid molecules that encode fragments, derivatives and analogues thereof. "Fragments" are intended to encompass all parts of the (poly)peptide that retain its biological activity. "Fragments" can consist of one sequence of consecutive amino acids or of more than one of such sequences. "Derivatives" are the complete (poly)peptide having CHIPS activity or fragments thereof that are modified in some way. Examples of modifications will follow hereinbelow. "Analogues" are similar (poly)peptides having CHIPS activity isolated from other organisms, in particular other pathogenic organisms. All of the above categories have one thing in common, namely that they have "CHIPS activity". CHIPS activity can be measured by any assay that shows directed migration of leukocytes towards an appropriate chemotactic stimulus. Examples of such assays include the under agarose technique (as exemplified in Balasoiu, et al., Diabetes care 20: 392-395 (1997)), modified Boyden chamber techniques and transwell systems. The latter technique is further illustrated in the examples.

Therefore, for the present application, the term "(poly) peptides having CHIPS activity" is intended to include the original CHIPS protein, (poly)peptides, fragments, derivatives and analogues that exhibit CHIPS activity.

The isolated nucleic acid molecule according to the invention may be DNA, RNA or cDNA.

The invention furthermore relates to probes and primers derived from the nucleic acid molecule of the invention. Such primers are oligonucleotides or polynucleotides of at least about 10 consecutive nucleotides (nt), and more preferably at least about 25 nt, still more preferably at least about 30 nt, and even more preferably about 30-70 nt of the nucleic acid molecule of the invention. Probes are longer and may for instance be a portion of the nucleic acid molecule of the invention of 50-300 consecutive nt, or even as long as the entire nucleic acid molecule.

Such oligonucleotides or polynucleotides are useful as diagnostic probes or as probes in conventional DNA hybridisation techniques or as primers for amplification of a target sequence by polymerase chain reaction (PCR) as described for instance in Ausubel et al. (supra)

Furthermore, the invention relates to a recombinant vector comprising at least one isolated nucleic acid molecule of the invention. The vector to be used can be selected by the skilled person based on his common general knowledge and will be dependent on the host that is used.

In addition to vectors, the invention provides for a bacteriophage comprising at least one isolated nucleic acid of the invention. In most CHIPS-positive Staphylococci, the gene encoding CHIPS is located on a prophage and can be turned into an active phage, for example by treatment with mitomycin according to standard and published, phage isolating procedures. A bacteriophage is thus a useful vehicle to introduce the CHIPS gene into a host.

The invention in addition relates to a method for making a recombinant vector, comprising inserting at least one isolated nucleic acid molecule of the invention into a vector. By incorporating more than one copy in the vector, or introducing more than one vector into a host the level of expression can be influenced. When a host cell is used that comprises an endogenous gene for a corresponding (poly) peptide having CHIPS activity, the expression level thereof can be increased by introducing more copies of the nucleic acid molecule (i.e. the gene) into the host cell or changing the promoter or regulator regions.

The invention thus also relates to recombinant hosts comprising at least one isolated nucleic acid molecule or vector of the invention. A number of types of organisms or cells from prokaryotes, protista, fungi, animals or plants may act as suitable host for the expression of recombinant (poly)peptides having CHIPS activity. Host cells include the widely used bacterial strain *Escherichia coli* including, but not limited to, the trc expression system (Brosius et al., supra) that allows high-level, regulated expression from the trc promotor. Potentially suitable other bacterial strains include Gram-positive bacterial strains, such as *Bacillus subtilis, Staphylococcus aureus*, or any bacterial strain capable of expressing heterologous proteins. A preferred production process in *E. coli* is given in Example 6.

The (poly)peptide having CHIPS activity may also be produced as a recombinant protein using a suitable expression system employing lower eukaryotes such as yeast or insect cells. Suitable yeast strains include *Saccharomyces cerevisiae, Pichia pastoris, Candida* or any yeast strain capable of expressing heterologous proteins. Insect cells used for recombinant protein expression include the *Drosophila* system and the Baculovirus system. Alternatively, it may be possible to produce the (poly)peptide having CHIPS activity in an mammalian expression system that includes several suitable host cells, including monkey COS cells, hamster CHO, BHK cells or RBL-2H3, human 293, 3T3, HeLa, U937, HL-60 or Jurkat cells, mouse L cells and other transformed cells for in vitro culture. For expression of (poly)peptides having CHIPS activity in eukaryotic systems, it may be necessary to modify the protein produced therein in order to obtain a functional protein. Such modifications, like attachments or substitutions may be accomplished using known chemical or enzymatic methods. In addition, the sequence of the nucleic acid molecule may be adapted to the codon usage of the host cell.

The (poly)peptide having CHIPS activity of the invention may also be expressed as a product of transgenic animals, e.g. as a component of the milk of transgenic cows, goats, pigs, sheep, rabbits or mice which are characterized by somatic or germ cells containing a nucleotide sequence encoding the (poly)peptide having CHIPS activity.

The (poly)peptide may be prepared by culturing transformed host cells under culture conditions suitable to express the recombinant protein. The resulting protein may then be purified from the culture medium or cell extracts using a purification process, for example comprising the steps of guiding over an absorption chromatography column the culture supernatant of the host cell or a liquid obtained therefrom after pre-purification; subsequently guiding the flow-through of the absorption chromatography column first over an affinity chromatography column and thereafter guiding the eluate of the affinity chromatography column over a DNA column; or subsequently guiding the flow-through of the absorption chromatography column first over a DNA column and thereafter guiding the flow-through of the DNA column over an absorption chromatography column; guiding the flow-through respectively the eluate of the last column of the previous step over a gel filtration column and Anion exchange column, selecting the fraction with a molecular weight of about 17 kDa and CHIPS activity. "Flow-through" is herein understood to mean that part of the loaded liquid having situated therein the constituents which come from the column without extra treatment. The constituents in this flow-through do not bind to the column. "Eluate" is understood to mean the liquid which comes from the column after elution and which contains the constituents from the liquid loaded on the column which were bound to the column and were released again therefrom by the elution. In this method the absorption column binds most constituents of the loaded culture medium or a liquid obtained therefrom after pre-purification. The affinity column binds the (poly)peptide having CHIPS activity and the Snase (Staphylococcal Nuclease) which has a similar molecular weight as the CHIPS protein and a similar affinity (or lack thereof) for the affinity column respectively the absorption column. The DNA column binds only the Snase. This method works particularly well if the first affinity chromatography column is a so-called Ligand Dye "yellow" column, the second affinity chromatography column is a so-called Ligand Dye "green" column and the DNA column a DNA cellulose column.

In addition, other known purification methods can be used, such as gel filtration, ion exchange chromatography, affinity chromatography, hydrophobic interaction chromatography or immunoaffinity chromatography.

Alternatively the (poly)peptide having CHIPS activity may be expressed in a form that will facilitate purification. For example, it may be tagged with a polyhistidine (6×His) epitope and subsequently purified by using a resin to which nickel ions are bound by means of a chelating agent. The (poly)peptide having CHIPS activity containing the tag is eluted from the resin by lowering pH or by competing with imidazole or histidine. Such epitope is commercially available from Invitrogen. Introduction of a protease cleavage site, like that for enterokinase, enables removal of the fusion tag to generate mature native recombinant (poly)peptide having CHIPS activity. Materials and methods for such an expression system are commercially available from Invitrogen, using the pTrcHis Xpress™ vectors in combination with ProBound™ resin for efficient isolation of His-tagged protein and EnterokinaseMax™ as highly catalytic active protease and EK-Away™ enterokinase affinity resin to remove the contaminating presence of the protease. Other tags known to those skilled in the art that can be used to facilitate purification include, but are not limited to, glutathion S transferase (GST fusion), myc and HA.

The (poly)peptide having CHIPS activity may also be produced by known chemical synthesis. Methods for constructing polypeptides or proteins by synthetic means are known to those skilled in the art. The synthetic protein, by virtue of sharing primary, secondary and tertiary structural and/or conformational characteristics with the corresponding (poly)peptide having CHIPS activity will posses an activity in common therewith, meaning CHIPS properties. Thus, such synthetically produced proteins can be employed as biologically active or immunological substitute for natural purified (poly)peptide having CHIPS activity. The synthesis of CHIPS is further illustrated in Example 7.

The (poly)peptides having CHIPS activity provided herein also include (poly)peptides characterized by amino acid sequences into which modifications are naturally provided or deliberately engineered. Modifications in the (poly) peptide or DNA sequences can be made by those skilled in the art using known conventional techniques. Modifications of interest in the CHIPS active (poly)peptide sequences may include replacement, insertion or deletion of selected amino acid residues in the coding sequence.

The information contained in the CHIPS protein, its gene and other (poly)peptides having CHIPS activity and their encoding nucleic acid molecules derived therefrom can be used to screen for fragments thereof or other agents which are capable of inhibiting or blocking binding of a (poly) peptide having CHIPS activity to leukocytes, and thus may act as inhibitors of chemotaxis activity and/or CHIPS binding to its putative receptor. Appropriate screening assays may for example use the fluorescent labeled purified CHIPS protein that binds to neutrophils as analyzed by flow cytometry or fluorometry. Example 2 describes such an assay. A suitable binding assay may alternatively employ purified CHIPS receptor or receptor domain on a carrier with a form of CHIPS protein as ligand. Alternatively, an assay can be employed that screens for the ability to bind or compete with CHIPS for binding to a specific anti-CHIPS antibody (monoclonal, polyclonal, or single chain antibody) by various immunoassays known in the art, including but not limited to competitive and non-competitive ELISA techniques or Biosensor technology employing a sensor chip coated with either ligand (CHIPS), antibody or putative CHIPS receptor (Surface Plasma Resonance (SPR) technique like the BiaCore). Any (poly)peptide having CHIPS activity other than CHIPS may also be used in the screening assays described. All these methods can be adapted for High Throughput Screening (HTS).

Isolated (poly)peptides having CHIPS activity may be used themselves as inhibitors of fMLP and C5a binding to their respective receptors FPR and C5aR, or to design inhibitors of CHIPS binding, by screening for competitive inhibition. Inhibitors of CHIPS binding (to the putative CHIPS receptor or receptor domains) are also useful for treating such conditions.

The invention furthermore relates to molecules that are not (poly)peptides themselves but have a structure and function similar to those of the (poly)peptides described herein. Examples of such molecules are peptidomimetics. When reference is made in this application to (poly)peptides, it is intended to include also such non-(poly)peptides that have a similar or the same structure and function and as a consequence a similar or the same biological activity as the (poly)peptides.

The functional activity of CHIPS, the (poly)peptides, their fragments, derivatives and analogues can be assayed by various methods. Preferentially, this CHIPS activity is measured by its ability to prevent the binding of fluorescent-fMLP (Bodipy-fMLP) or fluorescent-C5a (FITC-C5a) to neutrophils as determined by flow cytometry. Example 1 describes such an assay. CHIPS activity is also measured by its ability to prevent migration of neutrophils towards fMLP or C5a as determined by the Transwell chemotaxis assay, described in the Examples. Alternatively, an assay based on the ability of chemokines, including fMLP and C5a, to initiate a rapid and transient rise in intracellular calcium concentration can be employed to screen for CHIPS activity. Various assays known in the art can be used, including but not limited to the use of various calcium specific fluorescent probes in combination with flow cytometry or fluorometry, or microphysiometry. As cells for the screening of CHIPS activity by either method, freshly isolated neutrophils can be used or cells transfected with either FPR or C5aR, wild type or mutated forms of those receptors.

Isolated (poly)peptides having CHIPS activity may be useful in treating, preventing or ameliorating inflammatory conditions that are involved in many diseases and disorders, such as listed in Table 1. Support for the therapeutical usefulness of the (poly)peptides of the invention for treatment of the diseases in Table 1 can be found in the following references: For ARDS: Demling R H (1995). The modern version of adult respiratory distress syndrome. Ann. Rev. Med. 46:193-202; and Fujishima S, Aikawa N 1995 Neutrophil-mediated tissue injury and its modulation. Intensive Care Med 21:277-285; For severe infections (meningitis): Tunkel A R and Scheld W M (1993). Pathogenesis and pathophysiology of bacterial meningitis. Clin. Microbiol. Rev. 6:118. For injury after ischaemia/reperfusion: Helier T, et al. (1999). Selection of a C5a receptor antagonist from phage libraries attenuating the inflammatory response in immune complex disease and ischemia/reperfusion injury. J. Immunol. 163:985-994. For rheumatoid arthritis: Edwards S W and Hallett M B (1997). Seeing the wood for the trees: the forgotten role of neutrophils in rheumatoid arthritis. Immunology Today 18: 320-324; and Pillinger M H, Abramson S B (1995). The neutrophil in rheumatoid arthritis. Rheum. Dis. Clin. North Am. 1995 21:691-714. For myocardial infarction: Byrne J G, Smith W J, T Murphy M P, Couper G S, Appleyard R F, Cohn L H (1992). Complete prevention of myocardial stunning, contracture, low-reflow, and edema after heart transplantation by blocking neutrophil adhesion molecules during reperfusion. J. Thorac. Cardiovasc. Surg. 104:1589-96. For COPD: Cox G (1998). The role of neutrophils in inflammation. Can. Respir. J. 5 Suppl A:37A-40A; and Hiemstra P S, van Wetering S, Stolk J (1998). Neutrophil serine proteinases and defensins in chronic obstructive pulmonary disease: effects on pulmonary epithelium. Eur. Respir. J. 12:1200-1208. For stroke: Barone F C, Feuerstein G Z (1999). Inflammatory mediators and stroke: new opportunities for novel therapeutics. J. Cereb. Blood Flow Metab. 19:819-834; and Jean W C, Spellman S R, Nussbaum E S, Low W C (1998). Reperfusion injury after focal cerebral ischemia: the role of inflammation and the therapeutic horizon. Neurosurgery 43:1382-1396. For meningitis: Tuomanen E I (1996). Molecular and cellular mechanisms of pneumococcal meningitis. Ann. N.Y. Acad. Sci. 797:42-52.

TABLE 1

Inflammatory conditions as targets for CHIPS

| SYSTEM | DISEASE |
| --- | --- |
| cardiovascular | arteriosclerosis |
|  | sepsis |
|  | ischaemic shock |
|  | cardiopulmonary bypass |
|  | aortic surgery |
|  | heart transplantation |
|  | myocardial infarction |
| central nervous | bacterial meningitis |
|  | viral meningitis |
|  | multiple sclerosis |
|  | stroke |
|  | Alzheimer's disease |
|  | Brain tumour |
| gastrointestinal | pancreatitis |
|  | ulcerative colitis |
|  | Crohn's disease |
|  | alcoholic hepatitis |
|  | viral hepatitis |
|  | *Heliobacter pylori* gastritis |
|  | gastric carcinoma |
|  | hepatocellular carcinoma |
|  | peritonitis |
| skin | psoriasis |
|  | contact dermatitis |
|  | atopic dermatitis |
|  | cutaneous T-cell lymphoma |
|  | burns |

TABLE 1-continued

Inflammatory conditions as targets for CHIPS

| SYSTEM | DISEASE |
| --- | --- |
| genitourinary | urinary tract infection |
|  | glomerulonephritis |
|  | *Trichomonas vaginalis* infection |
|  | endometriosis |
| joints | rheumatoid arthritis |
|  | acute reactive arthritis |
|  | gout |
| respiratory | ARDS |
|  | COPD |
|  | idiopathic pulmonary fibrosis |
|  | cystic fibrosis |
|  | asthma |
|  | pleural emphema |
|  | metal fume fever |
|  | bacterial pneumonia |
|  | chronic bronchitis |
|  | hypersensitivity pneumonia |
|  | *Mycobacterium tuber.* infection |
|  | viral respiratory tract infection |
|  | allergic rhinitis |
|  | sinusitis |
|  | bronchogenic carcinoma |
| various | periodontitis |
|  | HIV infection |
|  | chronic lymph leukemia |
|  | acute transplant rejection |
|  | glomerulonephritis |
|  | frost bite |
|  | repetitive strain injury |

According to a further aspect thereof, the invention thus relates to (poly)peptides having CHIPS activity for use in diagnosis, prophylaxis or therapy, in particular for use in the treatment of acute and chronic inflammation reactions and HIV infection, more in particular for use in the treatment of Adult Respiratory Distress Syndrome (ARDS), ischaemic shock, traumatic brain injury, severe infections, myocardial infarction, stroke, vessel surgery, ulcerative colitis, Crohn's disease, Chronic Obstructive Pulmonary Disease (COPD), rheumatoid arthritis, dermatoses, multiple sclerosis, Alzheimer's disease, arteriosclerosis, repetitive strain injury (RSI), acute transplant rejection, burns, acute reactive arthritis, pancreatitis, vasculitis, glomerulonephritis, gout, frost bite and meningitis.

The invention furthermore relates to the use of the (poly) peptides having CHIPS activity for the manufacture of a preparation for diagnosis, prophylaxis or therapy, in particular for the treatment of acute and chronic inflammation reactions and HIV infection, more in particular for the treatment of the indications listed above.

Also part of the present invention are therapeutic compositions comprising a suitable excipient and the (poly) peptide having CHIPS activity of the invention. Such composition can be used for the treatments as specified above.

The invention further relates to use of the nucleic acid molecule of the invention, optionally incorporated in a larger construct, for various purposes, such as raising antibodies thereto, modulating the CHIPS activity or in a therapeutic preparation.

The invention further relates to nucleic acid molecules and the amino acid sequence encoded by the nucleic acid molecules that can be identified by so-called "computer cloning". More specifically, this technique comprises using (1) the nucleic acid sequence as depicted in FIG. 4, or fragments, derivatives and analogues thereof, or (2) the amino acid sequence as depicted in FIG. 5, or fragments, derivatives and analogues thereof, as a query for screening nucleic acid sequences or nucleic acid sequence databases, or protein sequences or protein sequence databases, using search algorithms that can identify regions with homology. Such algorithms are known to the person skilled in the art and include, but are not limited to, BLAST searches (Altschul et al., J. Mol. Biol. 215, 403-410 (1990)). The sequence databases that may be searched include, but are not limited to, the Genbank™ database and the Swissprot™ database. When using a BLAST search or modifications thereof, generally subjects that display homology can be identified, Identification is based on the value of the Score or the Smallest Sum Probability P(N). Homologues of the CHIPS nucleic acid sequence or (poly)peptide sequence are defined by a Score that is at least 200, preferably at least 400, more preferably at least 800, most preferably at least 1600. Alternatively, the P(N) value can be used for identification of homologous sequences. Homologues of the CHIPS nucleic acid sequence or (poly)peptide sequence are defined by a P(N) value that is smaller than 1e-3, preferably smaller than 1e-6, more preferably smaller than 1e-12, even more preferably smaller than 1e-24, most preferably smaller than 1e-48.

In a still further embodiment of the invention antibodies or biologically active fragments thereof specifically directed to the (poly)peptide of the invention and CHIPS-based, CHIPS receptor-blocking molecules are provided. Such CHIPS-based, CHIPS receptor-blocking molecules, and antibodies or biologically active fragments thereof and chimerics, single chains, and expression libraries may be used to neutralise the activity of the CHIPS protein or related (poly)peptides in prophylaxis or therapy, or may be used for diagnostic purposes to bind CHIPS or related (poly)peptides. Such antibodies and CHIPS-based, CHIPS receptor-blocking molecules are for example useful for the treatment of *Staphylococcus* infection. The invention also provides therapeutic compositions comprising a suitable excipient and one or more of these antibodies and/or biologically active fragments thereof.

"CHIPS-based, CHIPS receptor-blocking molecules" are molecules that compete with CHIPS in a CHIPS binding assay as described in Example 8. Such "CHIPS-based, CHIPS receptor-blocking molecules" may or example be molecules that have the same amino acid composition and amino acid sequence as CHIPS, but not the complete sequence. Such molecules can be single fragments of CHIPS, or may consists of multiple CHIPS fragments, all still having CHIPS activity. However, all other molecules that meet the functional requirement of competing with CHIPS in a CHIPS binding assay are also included.

The isolated nucleic acid molecules of the invention can furthermore be used for gene therapy. The nucleic acid molecule can be introduced at the site of inflammation to act locally or at a distant site. Gene therapy is via viral vectors, such as, but not limited to, adenoviral vectors, adeno-associated viral vectors or lentiviral vectors. Alternatively, non-viral vectors, such as those based on liposomes or polymers may be used. Gene therapeutic strategies are based on (1) in vivo gene therapy, where the isolated nucleic acid molecules of the invention are introduced into target cells in vivo, or (2) ex vivo gene therapy, where the isolated nucleic acid molecules of the invention are introduced into target cells ex vivo, followed by administration of the transduced cells, or a subpopulation of the transduced cells, into an individual.

The invention relates to a method for treating a subject suffering from inflammation by administering a therapeutically effective amount of a (poly)peptide of the invention and a method for gene therapeutically treating a subject suffering from inflammation by administering a therapeutically effective amount of a nucleic acid molecule, as well as a method for treating a subject suffering from *staphylococcus* infection by administering a therapeutically effective amount of an antibody and/or biologically active fragment thereof.

The nucleic acid molecules of the invention can be used in a method for isolating from an organism a gene encoding a protein having CHIPS activity, which method comprises screening of a genomic or cDNA library of that organism with a probe based on the nucleic acid molecule, and isolation of the positive clones.

According to a further aspect thereof, the invention relates to micro-organism harboring one or more nucleic acid molecules of the invention for use as a medicament for the treatment of acute and chronic inflammation reactions and HIV infection, in particular for treating Adult Respiratory Distress Syndrome (ARDS), ischaemic shock, traumatic brain injury, severe infections, myocardial infarction, stroke, vessel surgery, ulcerative colitis, Crohn's disease, Chronic Obstructive Pulmonary Disease (COPD), rheumatoid arthritis, dermatoses, multiple sclerosis, Alzheimer's disease, arteriosclerosis, repetitive strain injury (RSI), acute transplant rejection, burns, acute reactive arthritis, pancreatitis, vasculitis, glomerulonephritis, gout, frost bite and meningitis.

The invention further relates to a diagnostic PCR test for screening a patient infected with *Staphylococcus aureus* on the presence of the CHIPS gene. CHIPS is an important staphylococcal virulence factor, so patients with CHIPS containing Staphylococci are at higher risk for invasive diseases and might need different or additional treatment.

All molecules of the invention, i.e. nucleic acid molecules, (poly)peptides, non-(poly)peptides, fragments, derivatives and analogues, may find various other applications. Such applications include, but are not limited to:

Isolation of factors that can bind the above mentioned molecules. Examples of such factors being receptors and proteins. Such isolation can for instance be performed using the yeast two hybrid system or using tagged molecules of the invention as bait for fishing.

Design of peptoids and peptidomimetics.

Making phage display libraries, which can in turn be used for determining active domains, functional equivalents etc.

Identifying signal transduction pathways that are activated or inactivated by CHIPS and the molecules of the invention.

Assay for determination of the biological CHIPS activity (chemotaxis inhibition or chemokine receptor expression)

All molecules of the invention can be labeled in any way. Examples of labeling include but are not limited to fluorescence, biotin, radioactive labeling etc. Such labeled molecules can be used for screening of compounds that resemble or overlap with the biological activity of CHIPS, as well as identification of binding sites, both in vivo and in vitro, and for tracing CHIPS protein or nucleic acid in an organism.

It is clear that where reference is made herein to a (poly)peptide having a particular amino acid sequence, it is intended to also encompass (poly)peptides containing one or more amino acids that are chemically modified in a manner obvious to one skilled in the art, provided that such modification does not abolish the CHIPS activity.

The present invention will be further illustrated in the examples that follow and that are in no way intended to be limiting to this invention. In this description and the examples reference is made to the following figures and tables:

BRIEF DESCRIPTION OF THE DRAWINGS

FIG. 4 shows the sequence (SEQ ID NO. 4) of the chp gene from S. aureus Newman. The Shine Dalgarno sequence (AGGAGA) and the chp open reading frame (ORF) are underlined. The nucleotides encoding the mature protein are indicated by a double line. Diverging nucleotides in S. aureus 1690 sequence are indicated above the sequence.

FIG. 5 shows the amino acid sequence (SEQ ID NO. 5) deduced from the S. aureus Newman chp gene. The region matching the N-terminal 35 amino acids of CHIPS is underlined. Diverging amino acids in the S. aureus 1690 protein are indicated above the sequence.

Diverging amino acids in the S. aureus 1690 protein are indicated above the sequence.

Figure 6:
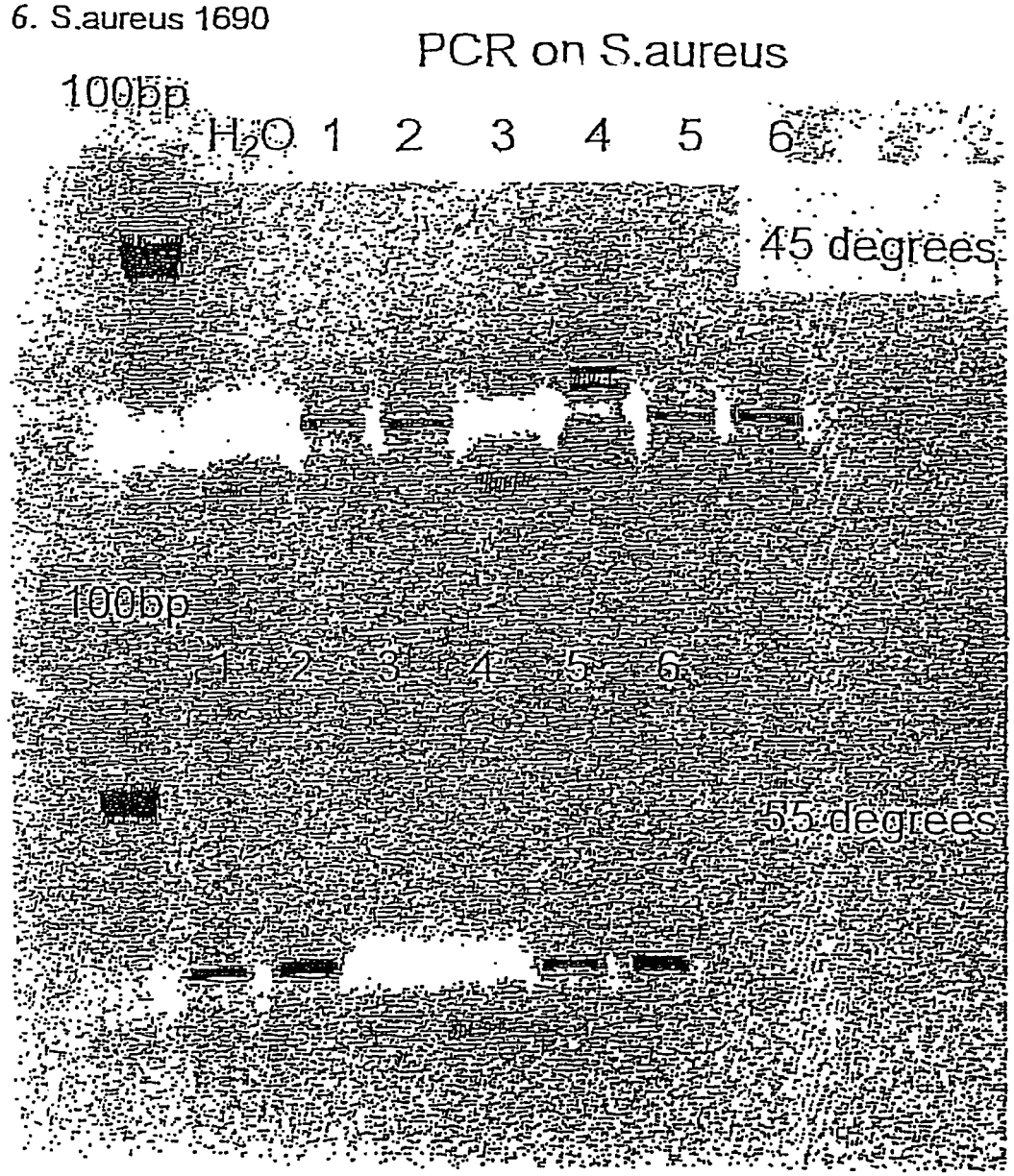

FIG. 6 shows the detection of the chp gene in the genomes of S. aureus strains in which the temperatures are applied to the annealing step of the PCR reactions.

Figure 7:
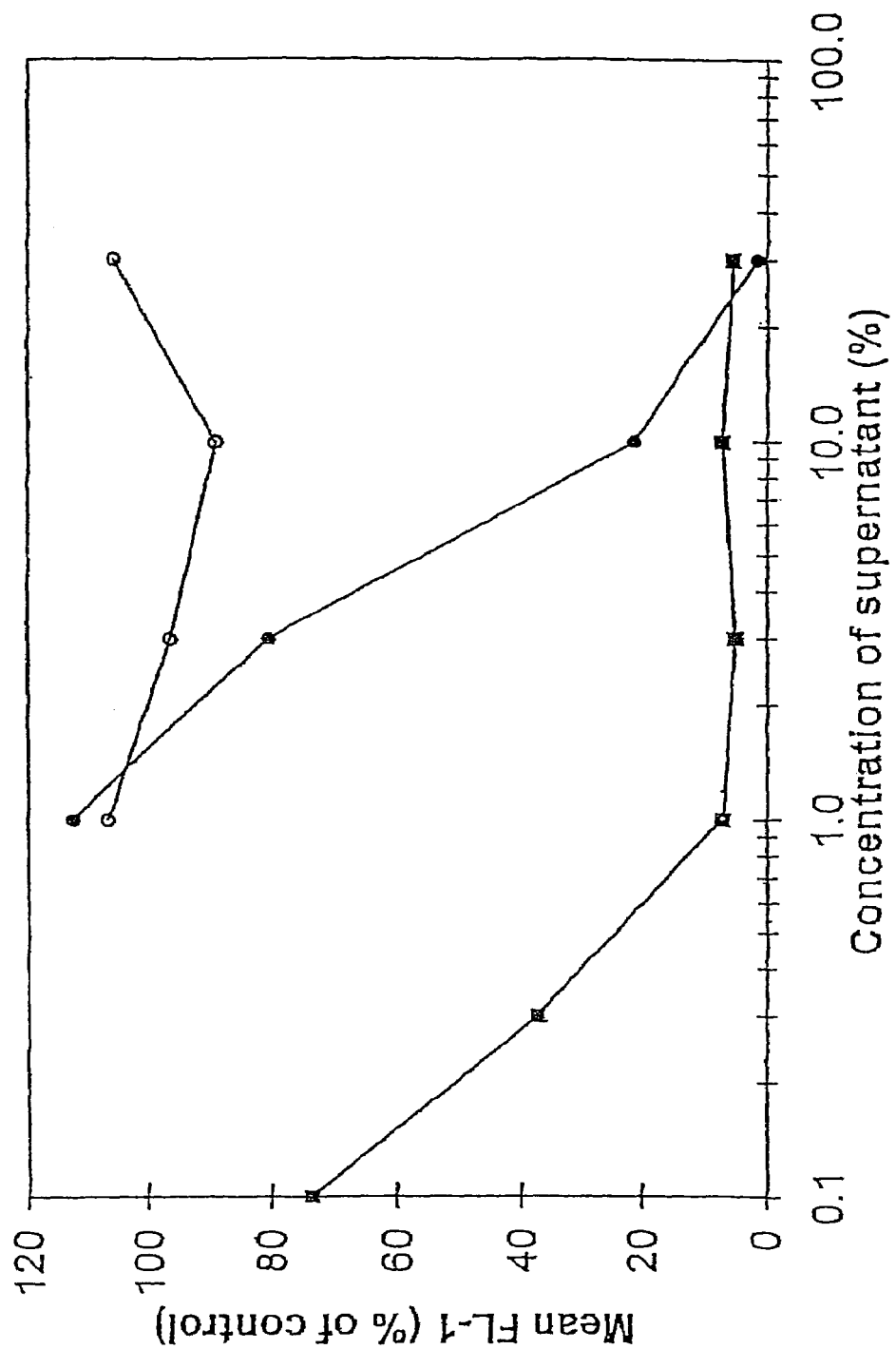

FIG. 7 shows CHIPS activity in the supernatants of S. aureus strains.

Figure 8:
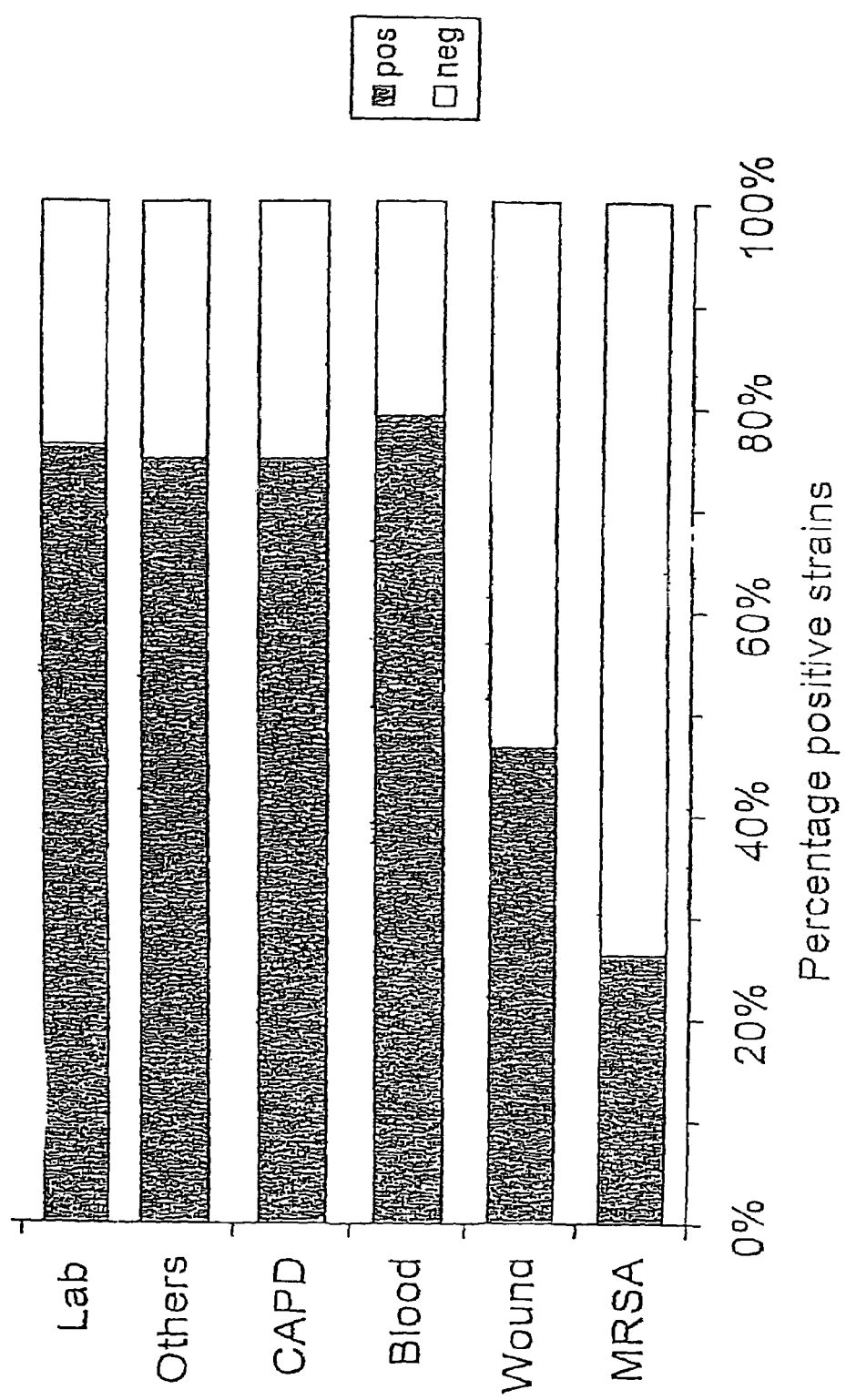

FIG. 8 shows the distribution of the chp gene in the genomes of various clinical S. aureus strains.

Figure 9A:
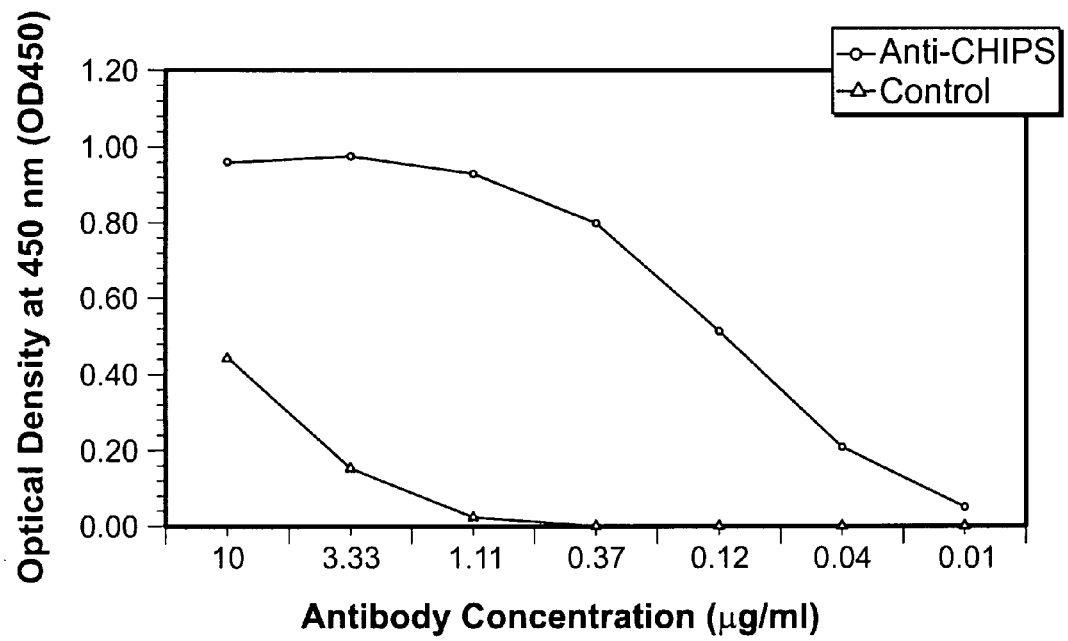
Figure 9B:
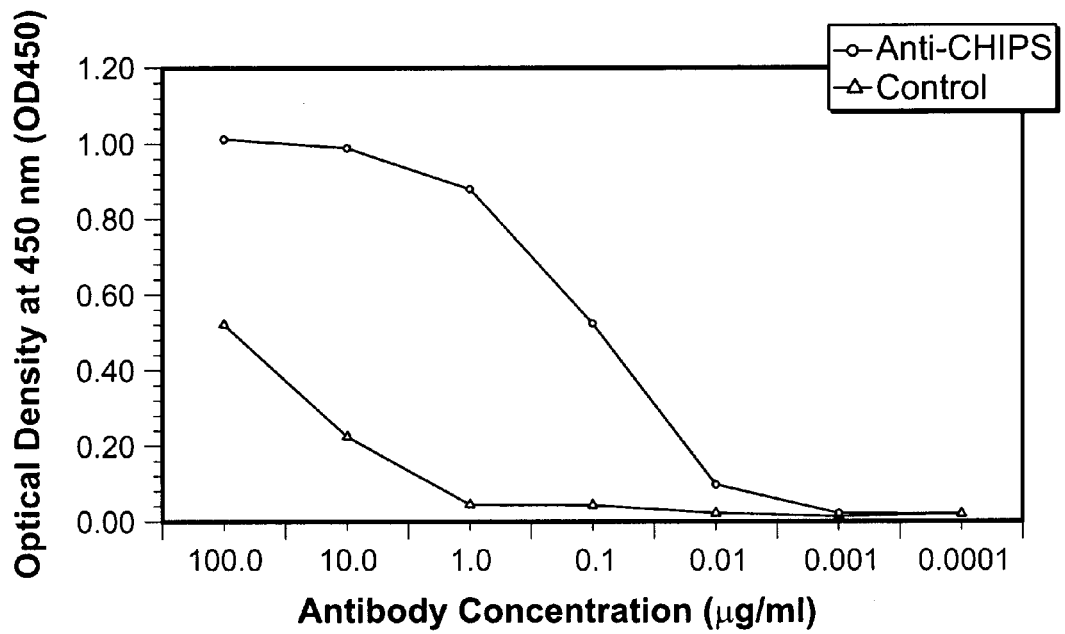

FIG. 9 shows two dose response curves of rabbit anti-CHIPS antibodies binding to CHIPS derived peptides of amino acids 1 through 15 (FIG. 9A) and purified CHIPS (FIG. 9B) as determined by ELISA.

Figure 10:
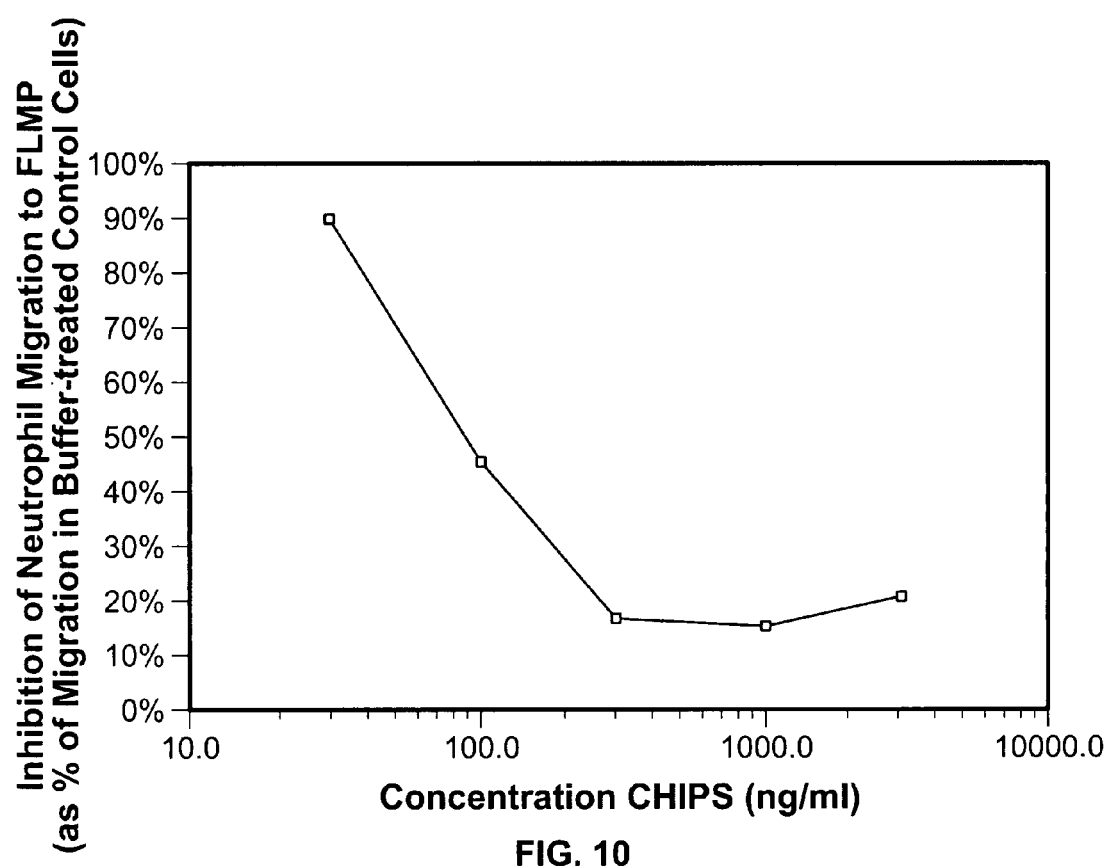

FIG. 10 shows the concentration dependent inhibition of neutrophil migration towards fMLP by purified CHIPS, expressed as percentage of buffer treated cells. Cells were incubated with various concentrations CHIPS for 30 min at room temperature and added to the upper compartment of the Transwell container. Migration towards $1\times10^{-8}$ M fMLP was determined after 60 minutes incubation at 37° C.

Figure 11:
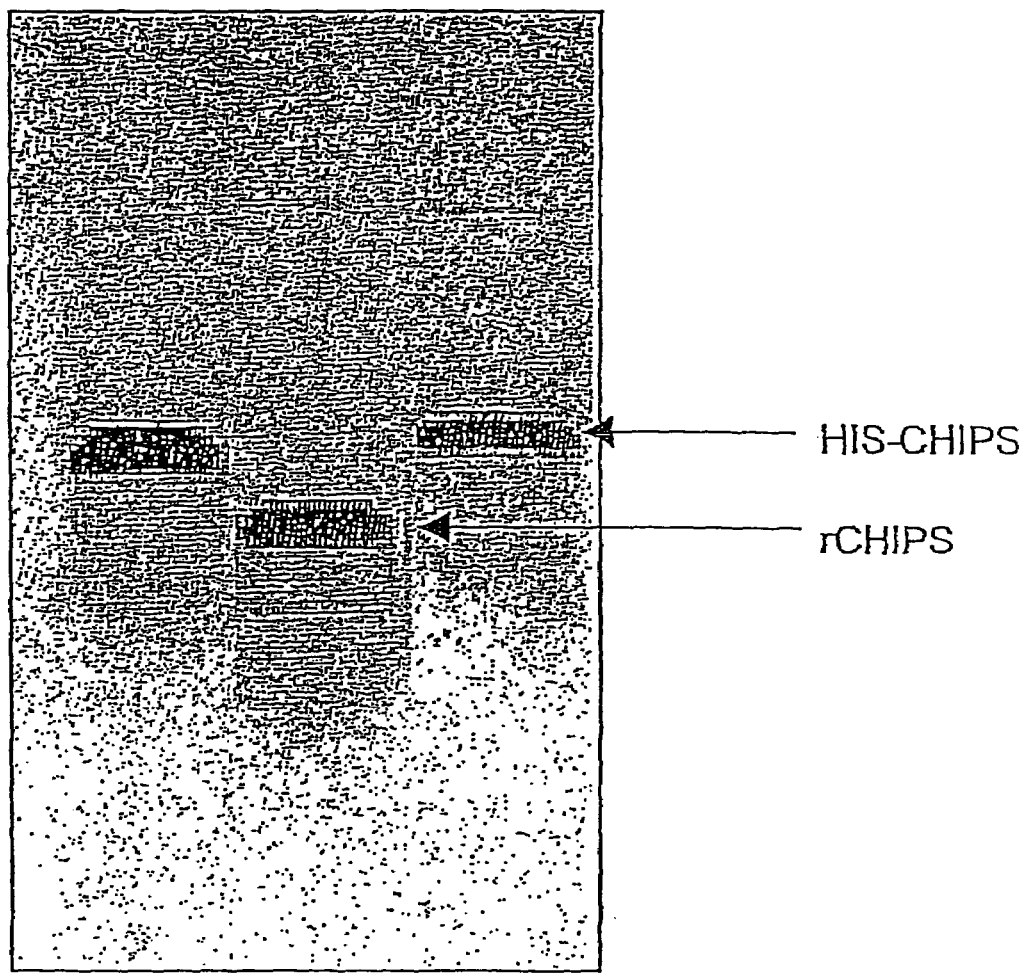

FIG. 11 is a representative image of an SDS-PAGE showing the final purified recombinant CHIPS (rCHIPS) obtained from an E. coli lysate after affinity chromatography over a Nickel column and cleavage of the Histidin tag by Enterokinase.

Figure 12:
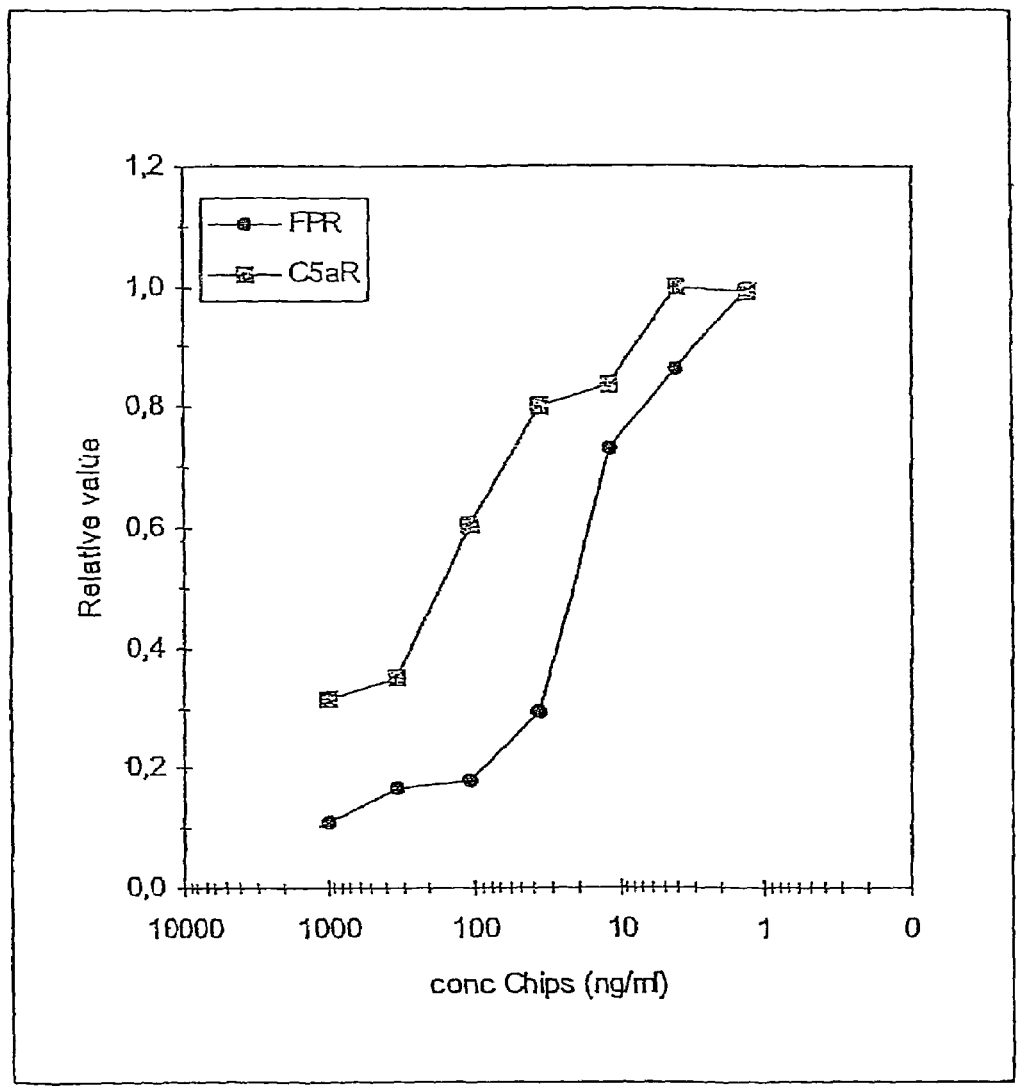

FIG. 12 shows the concentration dependent inhibition of recombinant CHIPS (Rchips) on the expression of the receptor for fMLP (FPR) and C5a (C5aR) on neutrophils.

Figure 13:
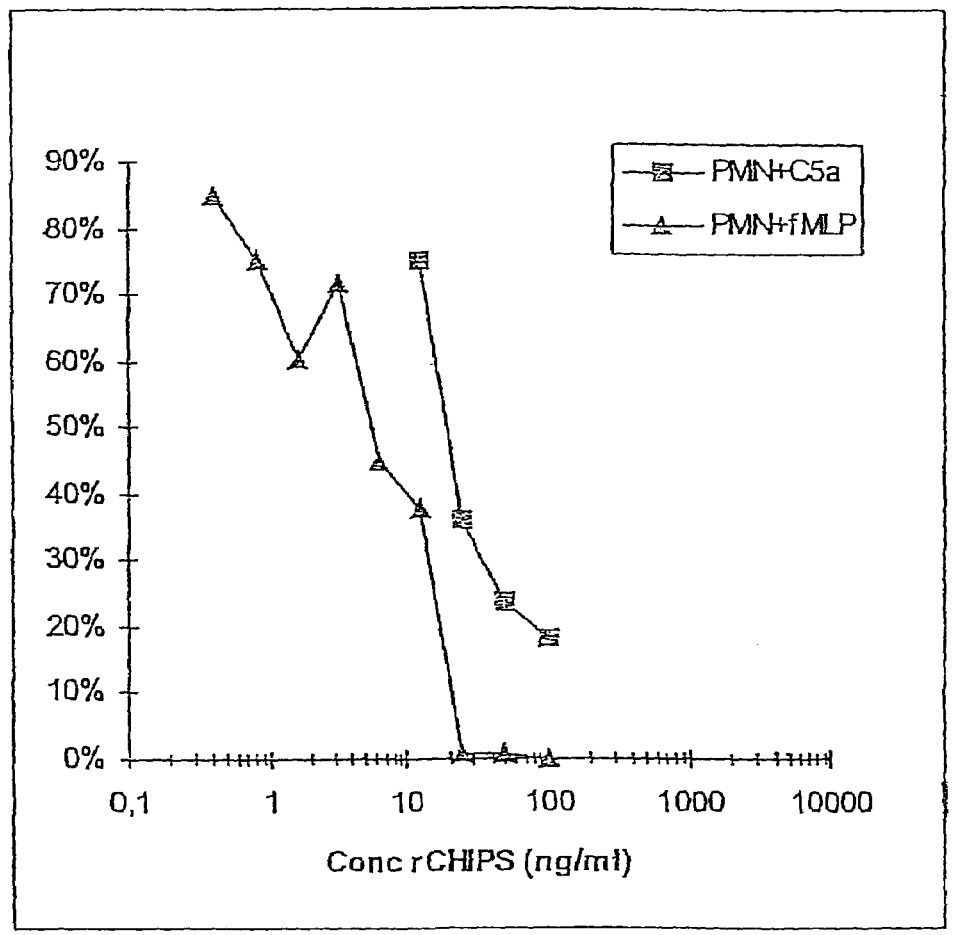

FIG. 13 shows the concentration dependent impairment of the intracellular free calcium release induced by fMLP and C5a in neutrophils.

Figure 14:
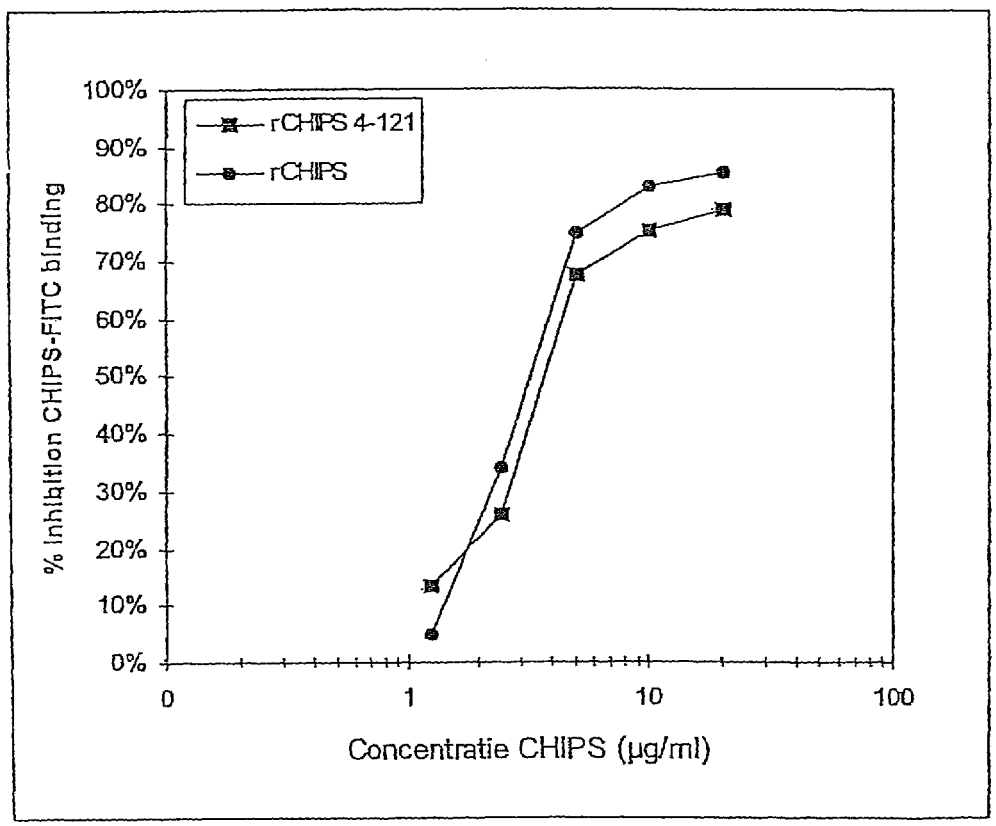

FIG. 14 shows the concentration dependent inhibition of CHIPS-FITC binding by the complete recombinant CHIPS and the recombinant mutant CHIPS$^{4-121}$.

BRIEF DESCRIPTION OF THE TABLES

Table 1 shows inflammatory conditions that can be treated with the (poly)peptides and non-(poly)peptides of the invention; and Table 2 shows the binding in ELISA of several selected clones of monoclonal antibodies derived from a mouse immunized with CHIPS. Binding is to purified CHIPS and the reacting mouse monoclonals are detected with a HRPO-coupled anti-mouse antibody.

EXAMPLES

Example 1

Purification of CHIPS Protein from S. aureus Supernatant

Material and Method 1.1 Isolation of the Protein

Staphylococcus aureus 1690 (a clinical isolate, University Medical Center Utrecht (UMC Utrecht)) or Staphylococcus aureus Newman (a gift from Dr Foster, Dublin) is cultured overnight in IMDM medium (Gibco) and subsequently diluted 1:40 in fresh IMDM for a 7 hour culture at 37° C. After pelleting of the bacteria the S. aureus supernatant (referred to as SaS) is collected, filtered over a 0.2 μm filter and immediately used further (Veldkamp et al., Inflammation 21. 541-551 (1997). A quantity of 5 liters of SaS is guided over three columns (25 ml) coupled in tandem. These three columns are successively a "Reactive Yellow" 861, ligand dye cross-linked 4% beaded agarose column (Sigma), a DNA Cellulose (Pharmacia) and a "Reactive Green" 19 ligand dye cross-linked 4% beaded agarose column (Sigma).

After washing with PBS the green (Reactive Green 19 column is eluted with 2 M NaCl and the second 50 ml, containing CHIPS activity, is pooled. PMSF (1 mM) is added and the eluate is dialysed in PBS for 18 hours. The sample is concentrated to a volume of ±10 ml in a dialysis bag soaked in polyethylene glycol. The concentrated material is separated on a Pharmacia Superdex-200 gel filtration column, whereafter the active fractions (4 ml volumes) are pooled, treated with PMSF (1 mM) and dialysed in 10 mM Tris-HCl (pH 8.0) for 18 hours. The pooled active fractions are loaded onto a Mono Q anion exchange column (Pharmacia) that is eluted with a gradient of 10 mM Tris-HCl buffer ranging from 0 to 1M NaCl. Active fractions (1 ml volumes) are pooled and used as the final preparation of purified CHIPS. Protein content is determined with a Pierce Micro-BCA assay and CHIPS is stored at −20° C. in small aliquots. The final isolated material is analysed for purity on a 12.5% SDS-PAGE (Mini-Protean II; BioRad) after staining with Coomassie Blue. The CHIPS protein appears as a single band with an apparent molecular weight around 17 kDa. All fractions are screened for CHIPS activity by its capacity to inhibit binding of fluorescent-labeled fMLP to isolated neutrophils as measured by flow cytometry.

1.2 Binding of fMLP and C5a to Granulocytes

Granulocytes are isolated from heparinized blood of healthy volunteers via a Histopaque-Ficoll gradient in accordance with the standard method (Troelstra et al., J. Leukocyte Biol. 61, 173-178 (1997)). The remaining erythrocytes in the granulocyte fraction are lysed with sterile water (for 30 sec.) and washed after recovery of the isotonicity. The cells are finally resuspended in PRMI (Gibco) with 0.05% Human Serum Albumin (RPMI/HSA). In Falcon tubes 50 μl cells ($5\times10^6$ cells/ml) are incubated with 50 μl CHIPS-containing material (SaS, purified CHIPS or column fractions) for 30 min at 37° C. The cells are placed on ice and washed once with RPMI/HSA (at 4° C.) and resuspended in 50 μl fresh medium. 5 μl BODIPY-labeled fMLP (final concentration 0.1 μM; Molecular Probes) or FITC-labeled C5a (final concentration 1 µM; recombinant C5a from Sigma, labeled with FITC as described in example 2.1 for CHIPS) is then added and the sample is incubated for 60 minutes on ice. After washing the fluorescent fMLP or C5a binding to the granulocytes is analysed with a flow cytometer (FACScan; Becton Dickinson). The average fluorescence value of 5000 granulocytes is calculated with Lysis II software.

Results

Figure 1:
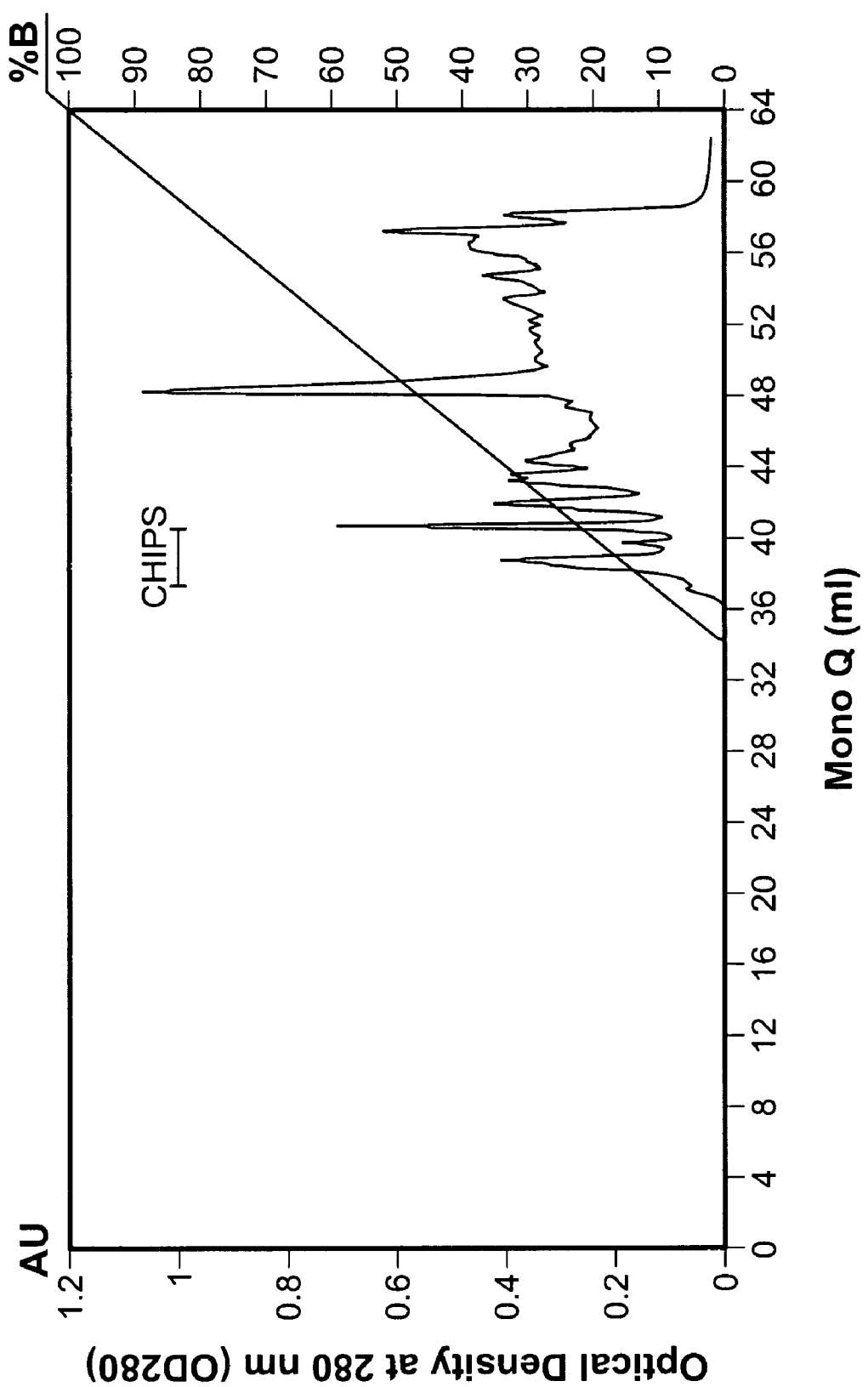
FIG. 1 shows the CHIPS activity of the eluate from the Mono Q column.
Figure 2:
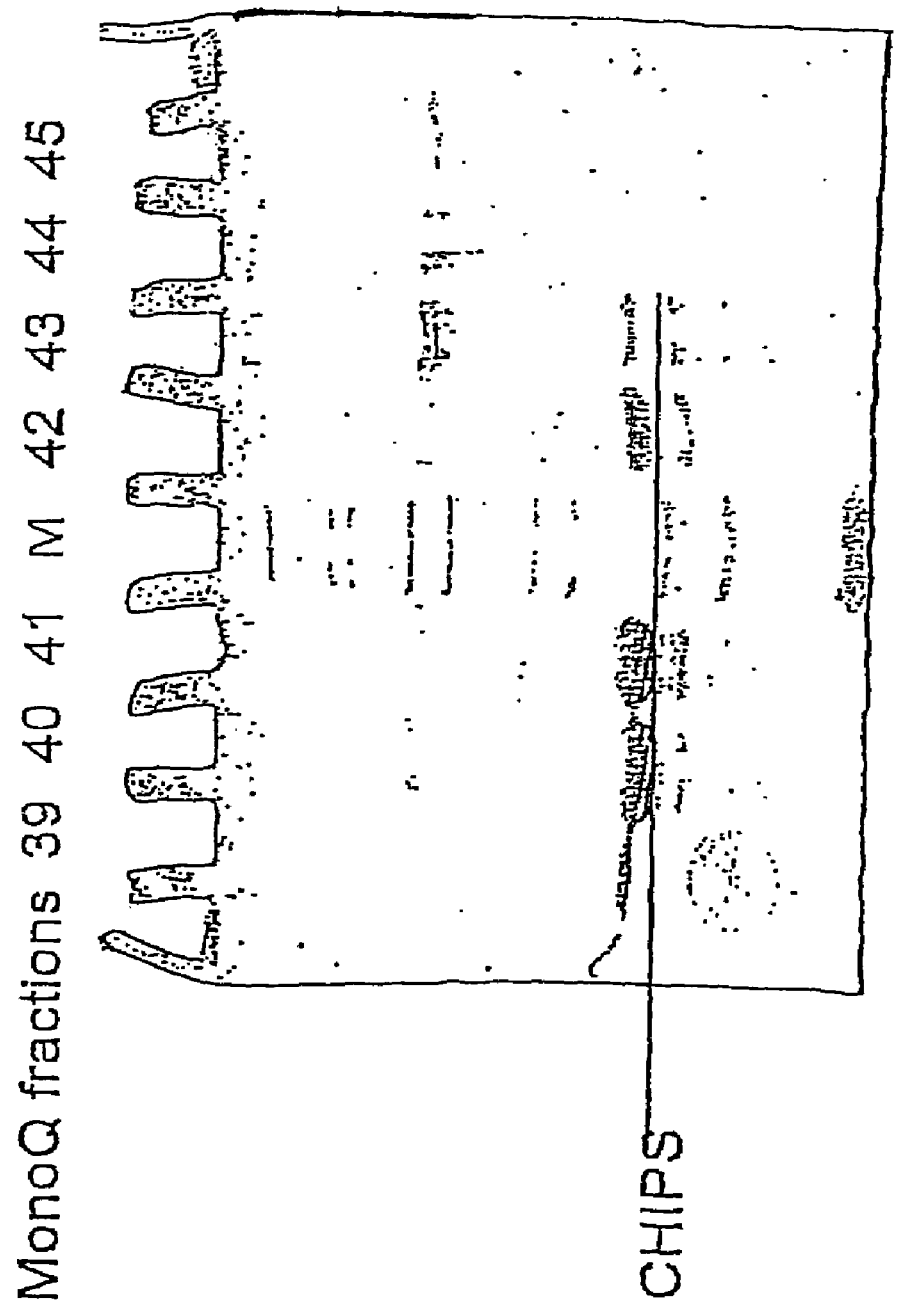
FIG. 2 shows the Coomassie Blue stained SDS-PAGE of purified CHIPS after the final Mono Q chromatography step.

FIG. 1 shows the elution profile (OD280) of the CHIPS activity of the eluate from the Mono Q column. The volume fractions between 39 and 41 ml show the strongest CHIPS activity. FIG. 2 shows the Coomassie Blue stained SDS-PAGE of purified CHIPS after the final Mono Q chromatography step.

Example 2

Specific Binding of CHIPS to Neutrophils and Monocytes

Material and Method 2.1 FITC Labeling of Purified CHIPS Protein

Purified CHIPS (500 µg/ml protein) is incubated with ⅒th volume of 1 mg/ml FITC (Fluorescein Isothiocyanate, Isomer I; Sigma) in a 1 M Sodium carbonate buffer pH 9.6 for 1 hour at room temperature. FITC-labeled CHIPS is separated from free FITC by passing the mixture over a desalting column (Pharmacia, Fast Desalting HR 10/10) and monitoring the eluate for $OD_{280}$ and fluorescence by an on-line coupled fluorometer (Perkin Elmer). Fractions with high $OD_{280}$ and fluorescence were pooled and analyzed for protein content with the Micro BCA protein assay (Pierce). CHIPS-FITC is stored in small aliquots at −20° C.

2.2 Binding of CHIPS-FITC to Leukocytes.

The specific binding of CHIPS-FITC to leukocytes is determined by flow cytometry. Purified neutrophils and mononuclear cells (consisting of monocytes and lymphocytes) are isolated from heparinized blood of healthy volunteers as described (Troelstra et al., Infect. Immun. 65: 2272-2277 (1997)). Isolated cells are remixed to obtain a ratio of cells that mimics the situation in blood. Human red blood cells are obtained by washing a small aliquot of whole blood thrice with PBS. The concentration of red blood cells is determined photospectrometrically.

In Falcon tubes 50 µl leukocytes or red blood cells ($5 \times 10^6$ cells/ml) are incubated with 5 µl CHIPS-FITC at various concentrations for 30 min on ice. Cells are washed once with medium (RPMI containing 0.05% HSA) and resuspended in 150 µl fresh medium. Binding of CHIPS-FITC to the leukocyte is measured by flow cytometry (FACScan; Becton Dickinson). Association with the various subpopulations is analyzed by selective electronic gating on forward (FSC) and sideward (SSC) scatter parameters in LysisII software (BD). The average fluorescence value of the selected cell population is calculated with the software.

Results

Figure 3:
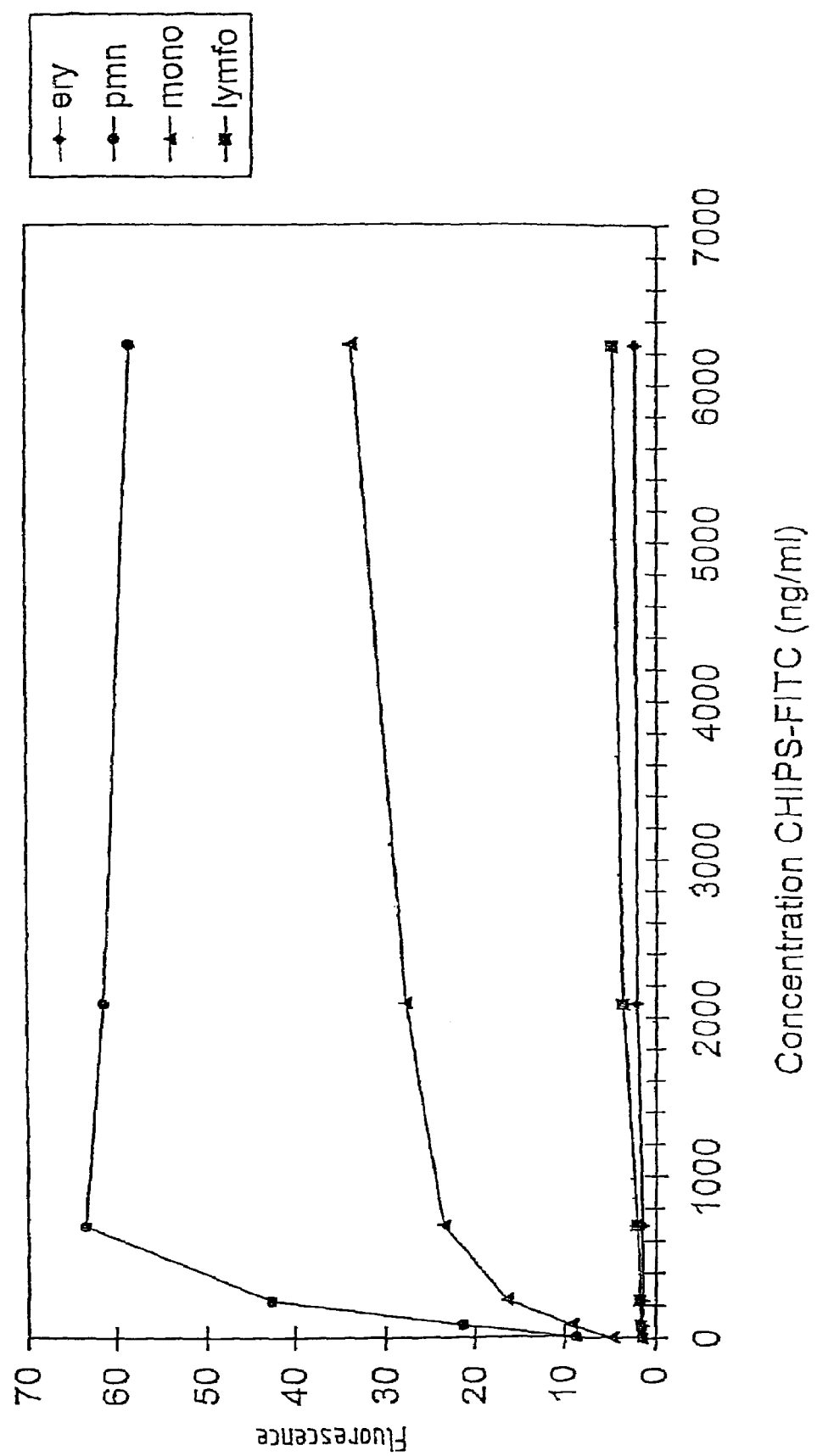
FIG. 3 shows the concentration dependent binding of CHIPS-FITX to the various leukocyte populations.

FIG. 3 shows the concentration dependent binding of CHIPS-FITC to the various leukocyte populations. It can be seen that CHIPS-FITC binds most efficiently to neutrophils, followed by monocytes. CHIPS-FITC does not bind to red blood cells and marginally to lymphocytes, but only to a subpopulation. Binding of CHIPS-FITC to neutrophils is specific because addition of a 10-fold excess of non-fluorescent labeled CHIPS completely inhibits association of CHIPS-FITC to the cells.

Example 3

Sequence, Cloning, and Expression of the CHIPS-encoding Gene (chp) of *Staphylococcus aureus*

Material and Method 3.1 Bacterial Strains, Plasmids and Growth Conditions

*Staphylococcus aureus* Newman, RN4220, and COL are commonly used laboratory strains. *S. aureus* 1690 is a clinical strain, isolated from a patient with bacteremia (K. E. Veldkamp et al., Inflammation, 21:541-551 (1997)). *Escherichia coli* DH5α was used as a cloning host (F. M. Ausubel et al., Current Protocols in Molecular Biology, John Wiley and Sons, Inc., New York, N.Y. (1990)). Plasmid pRB474 is a shuttle vector for *E. coli* and staphylococci containing the vegII promoter from *Bacillus subtilis* that permits expression of genes cloned into the multiple cloning site of pRB474. pRB474 is a derivative of pRB374 (R. Brückner, Gene, 122:187-192 (1992)) in which the neomycin resistance gene has been replaced by a chloramphenicol resistance gene. All strains were grown in BM broth (1% tryptone, 0.5% yeast extract, 0.5% NaCl, 0.1% $K_2HPO_4$, 0.1% glucose) at 37° C. unless otherwise noted.

3.2 Sequence Analysis

DNA was sequenced by cycle sequencing on a DNA sequencer 4000 L (LI-COR Inc., Lincoln, Nebr., USA) using the Thermo Sequenase™ fluorescent-labeled prime cycle sequencing kit (Amersham, Little Chalfont, UK). Suitable primers were used to directly sequence genomic DNA which was isolated according to J. Mamur (J. Mol. Biol., 3:208-218 (1961)). The sequencing method has been described briefly in Peschel et al. (J. Biol. Chem., 274:8405-8410 (1999)). To perform sequence similarity searches, the program BLAST 2.0 with the non-redundant protein database of the NCBI (Bethesda, Md., USA) was used. Sequence alignments were accomplished using the Higgins-Sharp algorithm of the program MacDNASIS Pro (Hitachi Software Engineering, San Bruno, Calif., USA).

Previously, the first 35 amino acids of CHIPS have been determined by N-terminal sequencing of the purified protein. The *S. aureus* DNA is very rich in A and T nucleotides while G and C nucleotides are rare (only about 30% of total bases). Thus, for most amino acids, the most A- and T-rich codons are preferred. According to this rule, a primer sequence was derived from amino acids 15-24 (GAAAAA-GAAAAGCATATAAAGAA (SEQ ID NO 1). The primer was used to directly sequence genomic DNA from *S. aureus* Newman yielding a sequence of several hundred base pairs. A new primer was derived from this sequence to read toward the binding site of the first primer. The combined DNA sequence contained the binding site of the first primer with two differences (G instead of A in position 3 and T instead of A in position 15) (FIG. 4). It encoded an open reading frame of 450 bp preceded by a reasonable Shine Dalgarno sequence for initiation of translation (J. Shine and L. Dalgarno, Proc. Natl. Acad. Sci. USA, 71:1342-1346 (1974)) and followed by three stop codons. The gene was named chp; it encodes a putative protein of 149 amino acids with no similarities to any protein in the databases. The N-terminal 28 amino acids seem to form a signal peptide for secretion across the cytoplasmic membrane (3 positively charged residues followed by a non-charged region of 22 amino acids and an ALA-X-ALA consensus motive for cleavage by the signal peptidase 1; FIG. 5) (G. von Heijne, Nucl. Acids Res. 14:4683-4690 (1986)). The signal peptide is followed by a region that matches almost perfectly the N-terminal 35 amino acids of CHIPS. The only exception is a serine in position 33 of the deduced mature protein instead of an asparagine residue predicted by N-terminal sequencing. The deduced mature protein has a size of 121 amino acids and 14.1 kDa and an isoelectric point of 9.32. It thus fulfills all requirements for the CHIPS protein. Using the same primers, the chp gene of *S. aureus* 1690 was sequenced. The two genes were almost identical with 5 deviations. On amino acid sequence level, only one position was exchanged (FIGS. 4 and 5).

3.3 Cloning and Expression of the chp Gene

The chp gene from *S. aureus* Newman was amplified by PCR using primers whose sequence was modified to introduce restriction sites permitting the cloning of chp in the expression plasmid pRB474. The resulting plasmid pPr4-chp contained the chp coding region, 19 bp upstream from the start codon containing the Shine Dalgarno sequence and 104 bp downstream from the first stop codon. The fragment was inserted in the appropriate orientation permitting expression of the gene by the vegII promoter and the identity of the fragment was verified by sequence analysis. Plasmid pPr4-chp was transferred to the restriction-negative strain *S. aureus* RN4220 by electroporation (J. Augustin and F. Götz, FEMS Microbiol. Lett. 66:203-208 (1990)), isolated from a positive clone, and electroporated into *S. aureus* COL (TIGR accession no. 1280). The identity of the plasmid was verified by restriction fragment analysis and sequencing of the insert.

The chp gene was not contained in the partly available genome sequence of *S. aureus* COL (TIGR accession no. 1280). By PCR analysis it was demonstrated, that the gene is in fact lacking in *S. aureus* COL while *S. aureus* Newman and 1690 were positive (FIG. 6). Furthermore, *S. aureus* COL was negative in the CHIPS activity assay (FIG. 7). The chp gene from *S. aureus* Newman was cloned in plasmid pPr4-chp, which permits expression of cloned genes by a plasmid-encoded promoter. Transformation of *S. aureus* COL with the plasmid rendered the strain positive in the CHIPS assay (FIG. 7), proving that the chp gene encodes the CHIPS protein.

3.4 Detection of the chp Gene by PCR

The absence or presence of the chp gene in various *S. aureus* strains was determined by PCR using crude cell extracts as a template source. One bacterial colony from a fresh agar plate was resuspended in 1.5 ml saline, sedimented, and resuspended in 100 µl of a lysis mix solution containing 10 mM Tris-HCl, pH 8.0, 50 mM NaCl, 0.1 mg iysostaphin/ml, and 0.1 mg achromopeptidase/ml. Samples were incubated at 37° C. for 30 min and then centrifuged. The clear supernatant was heated to 100° C. for 5 min and subsequently diluted by addition of 400 µl TE buffer (1 mM EDTA, 10 mM Tris-HCl, pH 8). 1 µl of the cell extracts were applied to PCR reactions using the -chp-specific primers chp-5' (GAAAAAGAAATTAGCAACAACAG (SEQ ID NO 2)) and chp-3' (CATAAGATGATTTAGACTCTCC (SEQ ID NO 3). Amplification was accomplished by 35 cycles composed of 1 min at 90° C., 1 min at 55° C., and 1 min at 72° C. The resulting PCR product comprised 90.4% of the chp gene starting 2 bp downstream of the start codon and ending 41 bp upstream of the first stop codon. The PCR products were subjected to agarose gel electrophoresis. All sequencing, PCR, and recombinant DNA techniques were carried-out according to standard procedures (F. M. Ausubel et al., Current Protocols in Molecular Biology, John Wiley and Sons, Inc., New York, N.Y. (1990)).

3.5 Assay for CHIPS Activity

*S. aureus* strains were analyzed for CHIPS activity in an assay for binding of fluorescence-labeled fMLP to human neutrophils. Strains were cultivated in IMDM medium (Life Technologies, Paisley, UK), for 24 h and culture supernatants were dialyzed and tested as described in example 1.2.

Results

FIG. 4 shows the sequence of the chp gene from *S. aureus* Newman. The Shine Dalgarno sequence (AGGAGA) and the chp open reading frame (ORF) are underlined. The nucleotides encoding the mature protein are indicated by a double line. Diverging nucleotides in *S. aureus* 1690 sequence are indicated above the sequence.

FIG. 5 shows the amino acid sequence deduced from the *S. aureus* Newman chp gene. The region matching the N-terminal 35 amino acids of CHIPS is underlined. Diverging amino acids in the *S. aureus* 1690 protein are indicated above the sequence.

FIG. 6 shows the detection of the chp gene in the genomes of *S. aureus* strains. PCR products obtained with chp-specific primers were separated on an agarose gel. Lanes 1 and 2, *S. aureus* Newman; lanes 3 and 4, *S. aureus* COL; lanes 5 and 6, *S. aureus* 1690. The following bacteria were found to be negative for the presence of the chp gene as determined by PCR: *Staphylococcus capitis, Staphylococcus haemolyticus, Staphylococcus hominis, Staphylococcus epidermidis, Staphylococcus saprophyticus, Staphylococcus warneri* and *Escherichia coli*.

FIG. 7 shows CHIPS activity in the supernatants of *S. aureus* strains. Various concentrations of culture supernatants of *S. aureus* 1690 (squares), COL wild-type (open circles) and COL with plasmid pPr4-chp (solid circles) were tested for inhibition of fMLP binding to human neutrophils. The background fluorescence was subtracted and values are given as % of the control samples (incubation without culture supernatants).

FIG. 8 shows the distribution of the chp gene in the genomes of various clinical *S. aureus* strains. Bacteria are screened by PCR with chp-specific primers and evaluated for the presence of the specific 400 bp band on an agarose gel. *S. aureus* strains are grouped on focus of isolation from the patients. Lab=Laboratory strains; Others=strains from other body fluids; CAPD=Chronic Ambulatory Peritoneal Dialysis cultures; Blood=blood cultures; Wound=wound infections; MRSA=Multiple Resistance *S. aureus* strains.

Example 4

Antibodies Specific for CHIPS

Material and Method 4.1 Immunization

Antibodies specific for CHIPS protein can be produced using purified natural or recombinant protein or sequence derived synthetic peptides, as antigen. Both polyclonal and monoclonal antibodies have been produced using standard techniques (as described in Harlow and Lane (1988), Antibodies, A Laboratory manual, Cold Spring Harbor Laboratory Press; and Erich, et al (1989), J. Immunol. 143: 4053-4060). On the basis of the first 15 amino acids, a synthetic peptide was made in accordance with standard Fmoc chemistry as described in De Haas et al., J. Immunol. 161:3607-3615. The peptide was coupled to Keyhole Limpet Hemocyanin in accordance with the Instructions of manufacturer (Pierce) and subcutaneously immunized with Freund's Complete Adjuvant, followed by two booster injections with Freund's Incomplete adjuvant.

Immunoglobulin's from the sera of immunized animals or hybridoma cell culture supernatants are isolated by affinity chromatography using commercial resins containing Protein A, Protein G or recombinations thereof (Pharmacia).

4.2 Enzyme Linked Immunosorbent Assay (ELISA)

Antisera and purified antibodies (IgG) are screened for reactivity with purified CHIPS protein or derived synthetic peptides by ELISA. Therefore the antigen is coated on a microtitre plate (Nunc 'Maxisorb') in a concentration of 1 to 3 µg/ml in a 0.1 M carbonate buffer pH 9.6 during 18 hours at 4° C. After washing, non occupied plastic is blocked with 5% BSA in PBS/Tween 20 (0.05%) for 1 hr at 37° C. Serial dilutions of the antibodies are made in PBS/Tween containing 2% BSA and incubated for 1 hr at 37° C. Bound antibodies are incubated with a 1/5000 diluted peroxidase labeled secondary antibody, either goat anti-rabbit IgG for polyclonal antibodies or goat anti-mouse IgG for monoclonal antibodies (both from Southern Biotechnology Associates, Inc.), for 1 hr at 37° C. Reactions are developed with TMB as substrate and the Optical Density (OD) was read at 450 nm.

Results

FIG. 9 shows the specific binding of polyclonal IgG from a rabbit immunized with a synthetic peptide comprising the first 15 N-terminal amino acids of CHIPS (anti-CHIPS-peptide). A high $OD_{450}$ is shown for the rabbit anti-CHIPS-peptide with the peptide (FIG. 9B) coated to the wells. The effect is concentration dependent and is already significant with a minimal concentration of 30 ng/ml IgG. A non-immunized pool of normal rabbit IgG gives some background binding, but only at high antibody concentrations, especially when purified CHIPS is coated to the ELISA plate.

Table 2 shows the specific binding of selected hybridoma clones derived from mice immunized with purified CHIPS protein.

TABLE 2

| clone name | $OD_{450}$ |
|---|---|
| background | 0.056 |
| 25-1 | 0.973 |
| 25-2 | 0.985 |
| 25-3 | 1.286 |
| 29-1 | 1.847 |
| 29-2 | 1.433 |
| 29-3 | 1.564 |
| 29-4 | 2.123 |

Example 5

Chemotaxis Assay

The CHIPS activity of (poly)peptides and non-(poly)peptides of the invention can for example be determined with the following assay.

In order to determine the directed migration use is for example made of a Transwell system (Costar) consisting of an upper compartment and a lower compartment separated by a 3 µm polycarbonate membrane. The granulocytes are labelled with BCECF (2-carboxyethyl-5-(and-6-) carboxyfluorescein; Molecular Probes), a fluorescent label which enters the cytoplasm of the cells. The cells ($5 \times 10^6$) are incubated for 20 minutes at 22° C. with 3 µM BCECF-AM (the acetomethyl ester of 2-carboxyethyl-5-(and-6-)-carboxyfluorescein), subsequently washed three times and resuspended to $5 \times 10^6$ cells/ml in RPMI/HSA. 100 µl of cells and the desired quantity of the CHIPS protein is introduced into the upper compartment of the Transwell system and the whole is suspended in the wells of a standard 24-well microtitre plate (Costar). Each well contains 600 µl RPMI/HSA with or without addition of the chemoattractant for testing. The chemoattractants are: recombinant C5a (Sigma), recombinant interleukin-8 (Pepro Tech), Platelet Activating Factor-16 (PAF-16; Calbiochem) or fMLP (Sigma). After 60 minutes incubation at 37° C. the Transwell container is lifted from the wells and the microtitre plate is analysed for fluorescence in a CyoFluorII (PerSeptiveBiosystems). The degree of fluorescence is a direct measure for the number of granulocytes which has migrated through the membrane and is expressed as a percentage of the fluorescence of the added number of cells.

Results

FIG. 10 shows the concentration dependent inhibition of neutrophil migration towards FLMP by purified CHIPS, expressed as percentage of buffer treated control cells.

Example 6

Production of Recombinant Polypeptide having CHIPS Activity in *E. coli*

CHIPS was produced in *E. coli* and was found to be biologically as active as the naturally occurring CHIPS from *S. aureus*.

The production method used for the production of recombinant CHIPS can also be used for other (poly)peptides having CHIPS activity. This production method is illustrated hereinbelow.

The DNA sequence for CHIPS from *S. aureus* is cloned into a suitable vector that enables efficient expression of CHIPS in competent *E. coli* host cells using conventional molecular biology techniques. The strategy used enables expression of the complete CHIPS protein linked to a removable HIS-tag at the N-terminus in the cytoplasm of *E. coli*. The trc Expression System (pTrcHIS B vector; Invitrogen) was used that enables expression of non-toxic proteins in *E. coli*. This system uses the trc promotor for high-level, regulated expression in any *E. coli* strain with a multicloning vector. The vector contains an N-terminal polyhistidine (6×His) tag for rapid purification, a Xpress epitope for easy detection with an anti-Xpress antibody and an Enterokinase cleavage site for removal of fusion tag.

*S. aureus* Newman chromosomal DNA was used as template for the PCR reaction using Pwo-DNA polymerase that results in a blunt ended PCR product. The primers used are CHIPS-TTT (starts exactly with the first amino acid of CHIPS (F) and CHIPS-TAA (containing a stop codon and a EcoRI-site).

The PCR product is digested with EcoRI and the pTrcHIS B vector with BamHI. The 5' overhang is removed with S1-nuclease to make the BamHI site blunt ended exactly where the enterokinase (EK) will digest the protein. Thereafter the vector is digested with EcoRI and ligated with the digested PCR product.

For transformation of the vector, TOP-10 *E. coli* is used (InVitroGen) using standard calcium precipitation (F. M. Ausubel et al., 1990, Current Protocols in Molecular Biology, John Wiley and Sons, Inc., New York, N.Y.). Clones are screened on ampicillin containing plates and proper ligation of CHIPS gene is verified by sequencing of the isolated plasmid (clone-29).

After expression of the CHIPS gene, the *E. coli* bacteria are lysed and the protein mixture is applied onto a Nickel-ion affinity column (ProBond). Therefore a culture of clone29 in LB medium+50 µg/ml ampicillin is initiated with 1 mM IPTG for 4 h at 37° C. Bacteria are centrifuged and the pellet resuspended in cold phosphate buffer pH 7.8 and stored at in −20° C. For cell lysis, lysozyme (100 µg/ml) is added for 15' on ice, tubes are sonicated, frozen in liquid $N_2$ and thawed in a 37° C. waterbath. This cycle of sonication/freeze/thaw is repeated 3 times.

Thereafter RNase and DNase (5 µg/ml) are added for 30' on ice. The mixture is centrifuged at 3000 g for 30' at 4° C. and filtered through a 0.45 µm filter. The final lysate is diluted 1:1 with cold Phosphate buffer pH 7.8 and run through a charged Nickel column (InVItroGen). The column is washed with phosphate buffer pH 7.8, with phosphate buffer pH 6.0 and with phosphate buffer pH 5.3. The bound CHIPS is eluted with 500 mM imidazole in pH 6.0 phosphate buffer.

The HIS-tag is removed by enterokinase cleavage followed by removal of the protease with an EK-Away enterokinase affinity resin. Therefore the eluate is dialysed overnight in cold digestion buffer (50 mM Tris-HCl, 1 mM $CaCl_2$ and 0.1% Tween-20, pH 8.0), filtered through a 0.45 µm filter and digested with 0.175 µl Enterokinase/ml HIS-CHIPS product. This amount of Enterokinase is batch-dependent and results in a partial digestion to avoid the generation of breakdown products. The digested product is dialysed against phosphate buffer pH 7.8 and passed over a fresh Nickel column to eliminate uncleaved His-tagged CHIPS (HIS-CHIPS); the run through is pure recombinant CHIPS (rCHIPS). Undigested HIS-CHIPS can be eluted again from Nickel column for a second digestion round. The Nickel column is finally washed with 50 mM EDTA, 0.5 M NaOH, water, 5 mg/ml $NiCl_2$, water and stored in 20% ethanol.

All steps in the isolation and digestion of HIS-CHIPS are checked by SDS-PAGE on a 16.5% Tris-Tricine Ready gel (BioRad). Samples are mixed 1:1 with sample buffer (200 mM Tris-HCl pH 6.8, 2% SDS, 40% glycerol, 0.04% Coomassie), boiled for 5 min and loaded on the gel. The HIS-tag of the expressed protein contains an X-press epitope that enables detection of the HIS-CHIPS product by Western blot using the anti-X-press antibody (Invitrogen). In addition, CHIPS is specifically detected with the polyclonal rabbit anti-CHIPS peptide antibody. Proteins are transferred to a nitrocellulose membrane, blocked with 4% gelatin in PBS and probed with the antibody and the appropriate secondary peroxidase labeled conjugate (Harlow & Lane, 1988, Antibodies: a laboratory manual, Cold Spring Harbor Laboratory).

The concentration dependent inhibition of recombinant CHIPS (rCHIPS) on the expression of the receptor for fMLP (FPR) and C5a (C5aR) on neutrophils was demonstrated as follows. Cells were incubated with various concentrations rCHIPS for 15 min at room temperature, put on ice and subsequently probed with either BODIPY-labeled fMLP (see Example 1.2) or a monoclonal antibody directed against the C5aR (clone 5 S/1, SeroTec) in combination with a secondary FITC-labeled goat-anti-mouse Ig (DAKO, 1:30). Finally cells were washed and analyzed for receptor expression in a FACScan by measuring the fluorescence of 5000 neutrophils. Receptor expression is compared to buffer treated cells and expressed as a relative value.

The concentration dependent impairment of the intracellular free calcium release induced by fMLP and C5a in neutrophils was tested as follows. Cells were loaded with a Calcium specific intracellular probe (Fluo-3, acetoxymethyl (AM) ester; Molecular Probes) and incubated with various concentrations rCHIPS for 15 min at room temperature. From each sample the initial fluorescence value was determined in the FACScan by measuring 2000 cells. Subsequently, stimulus was added ($10^{-9}$ M fMLP or $10^{-10}$ M rC5a) and the fluorescence intensity from the same sample was determined exactly 15 seconds after administration of the stimulus (the optimal time point for both agonists). Triggering neutrophils with fMLP or C5a initiates a rapid and transient increase in free intracellular Calcium concentration that is measured by an increase Fluo-3 fluorescence signal. From each activated sample, the initial basal fluorescence value is subtracted. Results are expressed as a percentage of buffer treated cells stimulated with either fMLP or C5a.

Results

FIG. 11 is a representative image of an SDS-PAGE showing the final purified recombinant CHIPS (rCHIPS). The two flanking lanes (1 and 3) show the complete recombinant product that is encoded by the vector generating the CHIPS protein with an additional Histidine tag and enterokinase cleavage site. This encodes for a protein with an apparent molecular weight of 21 kDa, while purified Enterokinase treated CHIPS runs at an apparent molecular weight of 17 kDa, equally as shown for natural purified CHIPS from *S. aureus* (see Example 1.1 and FIG. 2). The purified rCHIPS was characterized by MALDITOF MS and revealed a molecular mass of 14.12250, that is highly comparable with the predicted molecular mass of 14.12217 based on the CHIPS sequence.

FIGS. 12 and 13 illustrate the biological effectiveness.

Example 7

Production of a Synthetic CHIPS Protein

It was demonstrated according to the invention that it is possible to produce a synthetic polypeptide that has the exact same activity as natural and as recombinant CHIPS. The production process is as follows:

Synthesis of FTFEPFPTNEEIESNKKMLE-KEKAYKESFKNSGLPTTLGKLDERLRNYLKKG-TKNSAQFEKKVILTENKGYYTVYLN-PLAEDRKNVELLGKMYKTY-FFKKGESKSSYVINGPGKTNEYAY peptide by TGT resin having 9-fluorenylmethyloxycarbonyl-(SEQ ID NO: 5) and O t-but protected Tyrosine [Fmoc Tyr (t-but)] attached thereto (5 g, 0.3 mmol, NovaBiochem) was transferred to peptide synthesiser, and a solution of piperidine (12 ml) in dimethylformamide (DMF; 18 ml) was added to the resin. The solution was swirled for 1 hour and the resin washed with DMF (3×30 ml) followed by dichloromethane (DCM; 3×30 ml) and allowed to dry under vacuum for 5 minutes. The remainder of the amino acids were sequentially assembled employing standard Fmoc chemistry. Cleavage of the protein was accomplished by treating the protein resin with a solution of trifluoroacetic acid/tetraisopropylsilane/$H_2O$ [90:8:2 v/v/v] for 2.5 hours. The crude product (2.1 gms) was isolated by ether precipitation followed by purification by using High Performance Liquid Chromatography. The purified product was characterised by MALDI MS.

References describing similar methods are:
E Bayer et al., in: Peptides, Chemistry, Structure and Biology. Proceedings of the 13th American Peptide symposium. R S Hodeges and J A Smith (eds) ESCOM, Leiden, (1994) p. 156.
G Grübler et al., in: Innovation and perspectives in Solid Phase Synthesis 3rd International Symposium. R E Pron (ed) Mayflower Worldwide, Birmingham (1994) p. 517.

Example 8

Competition for CHIPS Binding to its Putative Receptor

Material and Method 8.1 Production of Recombinant CHIPS[4-121]

When several *E. coli* colonies containing the plasmid with recombinant CHIPS were analyzed for proper insertion of the chp gene by sequencing, several incomplete insertions were found. One of them that contains the complete HIS-tag, enterokinase cleavage site and the CHIPS protein minus the first three amino acids (CHIPS[4-121]; clone 19) was further propagated and purified as described for complete CHIPS (see Example 6).

8.2 Competition with CHIPS-FITC Binding

In Falcon tubes 5 µl serial dilutions of recombinant CHIPS or CHIPS[4-121] were prepared and mixed with 5 µl CHIPS-FITC (10 µg/ml; see Example 2). Thereafter 50 µl isolated neutrophils at $5 \times 10^6$ cells/ml are added and incubated for 30 min on ice. Cells are washed and analyzed for CHIPS-FITC binding by flow cytometry as described in Example 2.

Results

FIG. 14 shows the concentration dependent inhibition of CHIPS-FITC binding by both the complete recombinant CHIPS as well as the recombinant mutant CHIPS[4-121]. Both preparations show a similar inhibition pattern with equal effective concentrations.

Incorporated herein by reference and attached following the "Abstract of the Invention" is a Sequence Listing as required by U.S.C. § 1.821(c) and in compliance with U.S.C. § 1823(a)(1).

The invention claimed is:

1. An isolated polypeptide having the biological activity of chemotaxis inhibitory protein from *Staphylococcus aureus* ("CHIPS activity") on complement factor 5a (C5a)-binding, wherein the polypeptide is encoded by a nucleotide sequence selected from the group consisting of:
   a) a nucleotide sequence comprising the sequence of nucleotides 125-490 as depicted in FIG. 4 (SEQ ID NO: 4);
   b) nucleotide sequences encoding a polypeptide having CHIPS activity and having the amino acid sequence depicted in FIG. 5 (SEQ ID NO: 5); and
   c) nucleotide sequences having at least 90% sequence identity with any one of the nucleotide sequences in a) or b),
   wherein the polypeptide is not isolated from the natural producing host cell and wherein CHIPS activity is measured by the ability of the polypeptide to prevent the binding of the fluorescent-C5a to neutrophils as determined by flow cytometry.

2. The polypeptide according to claim 1, wherein the polypeptide is encoded by the nucleotides 125-490 of the sequence as depicted in FIG. 4 (SEQ ID NO: 4).

3. The polypeptide according to claim 1, wherein the polypeptide is able to prevent the binding of fluorescent formyl-methionyl-leucyl-phenylalanine (fMLP)-peptide or fluorescent-C5a to neutrophils as determined by flow cytometry.

4. A therapeutic composition in unit dosage form comprising a suitable excipient and the polypeptide according to claim 1.

5. An isolated polypeptide which is encoded by the nucleotide sequence consisting of nucleotides 41-490 of SEQ ID NO: 4.

* * * * *

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Primer sequence

<400> SEQUENCE: 1
gaaaaagaaa aagcatataa agaa                                              24

<210> SEQ ID NO 2
<211> LENGTH: 23
<212> TYPE: DNA
<213> ORGANISM: Artificial Sequence
<220> FEATURE:
<223> OTHER INFORMATION: chp-specific primer chp-5'

<400> SEQUENCE: 2
gaaaaagaaa ttagcaacaa cag                                               23

<210> SEQ ID NO 3
<211> LENGTH: 22
<212> TYPE: DNA
<213> ORGANISM: Artificial Sequence
<220> FEATURE:
<223> OTHER INFORMATION: chp-specific primer chp-3'

<400> SEQUENCE: 3
cataagatga tttagactct cc                                                22

<210> SEQ ID NO 4
<211> LENGTH: 602
<212> TYPE: DNA
<213> ORGANISM: Staphylococcus aureus
<220> FEATURE:
<221> NAME/KEY: exon
<222> LOCATION: (125)..(488)
<223> OTHER INFORMATION:

<400> SEQUENCE: 4
```

```
ataaatttaa atatagaatt taaggagaat taacatcatt atgaaaaaga aattagcaac      60
aacagtttta gcattaagtt ttttaacggc aggaatcagt acacaccatc attcagcgaa     120 agct ttt act ttt gaa ccg ttt cct aca aat gaa gaa ata gaa tca aat      169
     Phe Thr Phe Glu Pro Phe Pro Thr Asn Glu Glu Ile Glu Ser Asn
     1               5                   10                  15 aag aaa atg tta gag aaa gaa aaa gct tat aaa gaa tca ttt aaa aat      217
Lys Lys Met Leu Glu Lys Glu Lys Ala Tyr Lys Glu Ser Phe Lys Asn
                20                  25                  30 agt ggt ctt cct aca acg cta gga aaa tta gat gaa cgt ttg aga aat      265
Ser Gly Leu Pro Thr Thr Leu Gly Lys Leu Asp Glu Arg Leu Arg Asn
            35                  40                  45 tat tta aag aaa ggc aca aaa aat tct gct caa ttt gaa aaa atg gtt      313
Tyr Leu Lys Lys Gly Thr Lys Asn Ser Ala Gln Phe Glu Lys Met Val
        50                  55                  60 att tta act gaa aat aaa ggt tac tat aca gta tat ctg aat aca cca      361
Ile Leu Thr Glu Asn Lys Gly Tyr Tyr Thr Val Tyr Leu Asn Thr Pro
    65                  70                  75 ctt gct gaa gat aga aaa aat gtt gag tta cta ggt aaa atg tat aaa      409
Leu Ala Glu Asp Arg Lys Asn Val Glu Leu Leu Gly Lys Met Tyr Lys
80                  85                  90                  95 aca tac ttc ttt aaa aaa gga gag tct aaa tca tct tat gta att aat      457
Thr Tyr Phe Phe Lys Lys Gly Glu Ser Lys Ser Ser Tyr Val Ile Asn
                100                 105                 110 ggt cct gga aaa act aat gaa tat gca tac t aatagtagtt acataaatta      508
Gly Pro Gly Lys Thr Asn Glu Tyr Ala Tyr
            115                 120 aaaggtagat atttcttttt tatataaagg tttggcagac atttcataac ttgccaaacc    568
tttatatatc taattatcaa actgcactaa actt                                602

<210> SEQ ID NO 5
<211> LENGTH: 121
<212> TYPE: PRT
<213> ORGANISM: Staphylococcus aureus

<400> SEQUENCE: 5

Phe Thr Phe Glu Pro Phe Pro Thr Asn Glu Glu Ile Glu Ser Asn Lys
1               5                   10                  15

Lys Met Leu Glu Lys Glu Lys Ala Tyr Lys Glu Ser Phe Lys Asn Ser
            20                  25                  30

Gly Leu Pro Thr Thr Leu Gly Lys Leu Asp Glu Arg Leu Arg Asn Tyr
        35                  40                  45

Leu Lys Lys Gly Thr Lys Asn Ser Ala Gln Phe Glu Lys Met Val Ile
    50                  55                  60

Leu Thr Glu Asn Lys Gly Tyr Tyr Thr Val Tyr Leu Asn Thr Pro Leu
65                  70                  75                  80

Ala Glu Asp Arg Lys Asn Val Glu Leu Leu Gly Lys Met Tyr Lys Thr
                85                  90                  95

Tyr Phe Phe Lys Lys Gly Glu Ser Lys Ser Ser Tyr Val Ile Asn Gly
                100                 105                 110

Pro Gly Lys Thr Asn Glu Tyr Ala Tyr
            115                 120
```